United States Patent [19]
Yoon

[11] Patent Number: 5,431,635
[45] Date of Patent: Jul. 11, 1995

[54] SAFETY PENETRATING INSTRUMENT HAVING A TRIGGERED SAFETY MEMBER FOR ESTABLISHING AN ENDOSCOPIC PORTAL IN AN ANATOMICAL CAVITY WALL

[76] Inventor: InBae Yoon, 2101 Highland Ridge Dr., Phoenix, Md. 21131

[21] Appl. No.: 83,220
[22] Filed: Jun. 24, 1993

Related U.S. Application Data

[63] Continuation-in-part of Ser. No. 628,899, Dec. 18, 1990, Pat. No. 5,226,426, and a continuation-in-part of Ser. No. 817,113, Jan. 6, 1992, Pat. No. 5,350,393.

[51] Int. Cl.[6] ............................................. A61M 5/00
[52] U.S. Cl. ......................... 604/165; 604/274; 606/185
[58] Field of Search ............... 128/751, 752, 753, 754, 128/4, 6; 604/95, 158, 162, 163, 164, 165, 170, 272, 274, 280, 169; 606/167, 171, 185

[56] References Cited

U.S. PATENT DOCUMENTS

| | | |
|---|---|---|
| 1,087,845 | 2/1914 | Stevens . |
| 1,213,001 | 1/1917 | Philips . |
| 1,248,492 | 12/1917 | Hill . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,535,773 | 8/1985 | Yoon . |
| 4,601,710 | 7/1986 | Moll . |
| 4,654,030 | 3/1987 | Moll et al. . |
| 4,828,547 | 5/1989 | Sahi et al. . |
| 4,869,717 | 9/1989 | Adair . |
| 4,902,280 | 2/1990 | Lander . |
| 4,931,042 | 6/1990 | Holmes et al. . |
| 4,943,280 | 7/1990 | Lander . |
| 5,030,206 | 7/1991 | Lander . |
| 5,053,016 | 10/1991 | Lander . |
| 5,066,288 | 11/1991 | Deniega et al. . |
| 5,073,169 | 12/1991 | Raiken . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,152,754 | 10/1992 | Plyley et al. . |
| 5,158,552 | 10/1992 | Borgia et al. . |
| 5,207,647 | 5/1993 | Phelps . |
| 5,215,526 | 1/1993 | Deniega et al. . |
| 5,224,951 | 7/1993 | Freitas . |
| 5,224,952 | 7/1993 | Deniega et al. . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 11/1993 | Deniega . |
| 5,275,583 | 1/1994 | Crainich . |
| 5,312,354 | 5/1994 | Allen et al. ............... 604/157 |
| 5,318,580 | 6/1994 | Gresl, Jr. ............... 604/185 |

FOREIGN PATENT DOCUMENTS

| | | |
|---|---|---|
| 2544262 | 4/1977 | Germany . |
| 904635 | 8/1962 | United Kingdom . |
| 878265 | 11/1981 | U.S.S.R. . |
| 897224 | 1/1982 | U.S.S.R. . |
| 1435246 | 11/1988 | U.S.S.R. . |
| 9304632 | 3/1993 | WIPO . |
| 9304715 | 3/1993 | WIPO . |
| 9304716 | 3/1993 | WIPO . |
| 9317626 | 9/1993 | WIPO . |

Primary Examiner—Stephen C. Pellegrino
Assistant Examiner—Guy V. Tucker

[57] ABSTRACT

A safety penetrating instrument for establishing a portal in an anatomical cavity for performing endoscopic procedures includes a penetrating member received within a portal sleeve for introducing the portal sleeve through a cavity wall into the anatomical cavity, a distally biased safety member having a distal end movable between an extended position protecting a sharp tip of the penetrating member and a retracted position exposing the sharp tip, a handle for manually moving the safety member to the retracted position and a locking and releasing mechanism for locking the safety member in the retracted position and releasing the safety member to return to the extended position in response to distal movement of an operating member upon penetration of the safety penetrating instrument into the anatomical cavity, the operating member being preferably carried by the penetrating member.

24 Claims, 19 Drawing Sheets

SAFETY PENETRATING INSTRUMENT HAVING A TRIGGERED SAFETY MEMBER FOR ESTABLISHING AN ENDOSCOPIC PORTAL IN AN ANATOMICAL CAVITY WALL

CROSS REFERENCE TO RELATED APPLICATIONS

This application is a continuation-in-part of application Ser. No. 07/628,899, filed Dec. 18, 1990, now U.S. Pat. No. 5,226,426, and patent application Ser. No. 07/817,113, filed Jan. 6, 1992, now U.S. Pat. No. 5,350,393, the disclosures of which are incorporated herein by reference.

BACKGROUND OF THE INVENTION

1. Field of the Invention

The present invention pertains to safety penetrating instruments and, more particularly, to safety penetrating instruments for use in forming portals for endoscopic procedures having safety members spring biased to an extended protruded position to protect against inadvertent contact with tissue of sharp penetrating members.

2. Discussion of the Prior Art

Safety penetrating instruments are widely used in medical procedures to gain access to anatomical cavities for performing endoscopic procedures, particularly laparoscopic procedures in the anatomical cavity. A well accepted type of safety penetrating instrument, as exemplified by U.S. Pat. No. 4,535,773 to Yoon, the Endopath trocar marketed by Ethicon EndoSurgery and the Surgiport trocar marketed by United States Surgical Corporation, includes a portal sleeve or cannula, a penetrating member received in the portal sleeve and a safety shield spring biased to move to an extended, protruding position to cover the sharp tip of the penetrating member once the penetrating member has entered the anatomical cavity. Accordingly, the safety shield protects tissue and organ structures within the anatomical cavity from accidental injury by contact with the sharp tip of the penetrating member after penetration or puncture of the anatomical cavity wall.

When the penetrating procedure is commenced, the distal end of the safety penetrating instrument is placed in contact with the anatomical cavity wall; and, as force is exerted on the safety penetrating instrument, contact of the safety shield with the cavity wall moves the safety shield proximally to a retracted position against the spring bias to expose the sharp tip of the penetrating member to permit the sharp tip to penetrate the cavity wall. Accordingly, the force required to penetrate the cavity wall includes not only the force required to pass the safety penetrating instrument through the anatomical cavity wall but also the force required to overcome the spring bias on the safety shield. Once the sharp tip of the penetrating member has entered the cavity, the spring bias on the safety shield overcomes the reduced proximal force on the safety shield causing the safety shield to move distally to the extended, protruding position, In practice, however, a residual proximal force is still applied to the safety shield after penetration of the sharp tip into the cavity due to contact with surrounding tissue and/or tissue trapped between the safety shield and the portal sleeve and/or the penetrating member, and the residual force is capable of preventing distal movement of the safety shield to the extended position. To assure distal movement of the safety shield upon entry of the safety penetrating instrument into the anatomical cavity, the strength of the spring biasing the safety shield distally can be increased; however, increasing the strength of the bias spring also increases the force required to penetrate the cavity wall which is undesirable. Accordingly, currently available safety penetrating instruments with safety shields utilize bias springs of strengths compromising force-to-penetrate and assured safety shield distal movement in an attempt to satisfy both requirements.

In order to provide surgeons with a sense of security, currently available safety penetrating instruments with safety shields utilize a mechanism for locking the safety shield in the distally protruded position after entry into the anatomical cavity; however, the need for a locking mechanism from a purely medical standpoint is not well established in that it is possible that a locked safety shield could cause damage upon inadvertent contact with tissue whereas an unlocked safety shield would move proximally against the spring bias like a shock absorber. It would be desirable to provide a safety penetrating instrument that provides both a sense of security to the surgeon and a shock absorbing effect.

Another type of safety penetrating instrument is exemplified by the Woodford Spike marketed by Dexide, Inc. wherein a cannulated penetrating member is disposed within a portal sleeve and a safety probe is disposed within the penetrating member and spring biased distally to extend beyond the sharp distal tip of the penetrating member upon entry into an anatomical cavity to provide a measure of protection against incidental contact with tissue within the anatomical cavity by the sharp tip of the penetrating member. Accordingly, the bias spring strength for the safety portal must be selected to compromise both force-to-penetrate and assured distal movement in the same manner as discussed above with respect to safety penetrating instruments with safety shields.

SUMMARY OF THE INVENTION

Accordingly, it is a primary object of the present invention to improve safety penetrating instruments of the type having a penetrating member and a safety member biased distally to protrude beyond the distal end of the penetrating member by easing penetration and assuring protrusion of the safety member.

Another object of the present invention is to reduce the force-to-penetrate required to penetrate an anatomical cavity wall with a safety penetrating instrument of the type having a distally biased safety member with a blunt distal end for protruding beyond a sharp distal end of a penetrating member once penetration into the cavity has been achieved.

A further object of the present invention is to increase the force biasing a safety member distally in a safety penetrating instrument to assure protrusion of the safety member after penetration into an anatomical cavity without increasing the force-to-penetrate required for penetration.

The present invention has an additional object in that a distally biased safety member is locked in a retracted position to expose a sharp distal end of a penetrating member prior to contacting a wall of an anatomical cavity to be penetrated and is released to allow movement of the safety member to an extended position upon penetration into the anatomical cavity.

Another object of the present invention is to trigger release of a distally protruding safety member in response to distal movement of a penetrating member upon penetration into an anatomical cavity.

A further object of the present invention is to utilize a strong spring to distally bias a safety member in a safety penetrating instrument to provide a shock absorber or cushion action without increasing the force-to-penetrate of the safety penetrating instrument.

Some of the advantages of the safety penetrating instrument of the present invention over the prior art are that the distal biasing force on a safety member can be designed to assure protrusion of the safety member upon penetration regardless of the anatomical cavity being penetrated, that the force-to-penetrate of a safety penetrating instrument can be reduced to permit use in delicate tissue, that the safety penetrating instrument can be used as a standard trocar, a standard safety shielded trocar or a triggered safety shielded trocar without requiring a complex mechanism, and that the safety penetrating instrument can be inexpensively manufactured with minimum components to reduce cost, facilitate sterilization for reuse and allow economical single patient use.

The present invention is generally characterized in a safety penetrating instrument for establishing a portal in a wall of an anatomical cavity for performing endoscopic procedures including a portal sleeve having a distal end for positioning in the anatomical cavity and a proximal end for positioning externally of the anatomical cavity wall, a penetrating member disposed in the portal sleeve having a sharp distal end for penetrating tissue, a safety member having a distal end and being movable relative to the penetrating member between an extended position where the safety member distal end protrudes distally of the penetrating member sharp distal end and a retracted position where the safety member distal end is disposed proximally of the penetrating member sharp distal end to expose the penetrating member sharp distal end, bias means for biasing the safety member to move distally toward the extended position and for permitting the safety member to move proximally toward the retracted position, a handle coupled with the safety member for moving the safety member to the retracted position, locking means for engaging the safety member to lock the safety member in the retracted position and releasing means including an operating member responsive to entry of the safety penetrating instrument into the anatomical cavity for triggering release of the locking means to permit the bias means to move the safety member to the extended position.

The above and still further objects, features and advantages of the present invention will become apparent from the following description of the preferred embodiments when considered in conjunction with the accompanying drawings wherein like reference numerals in the various figures are utilized to designate like components.

DESCRIPTION OF THE PREFERRED EMBODIMENT

Figure 1:
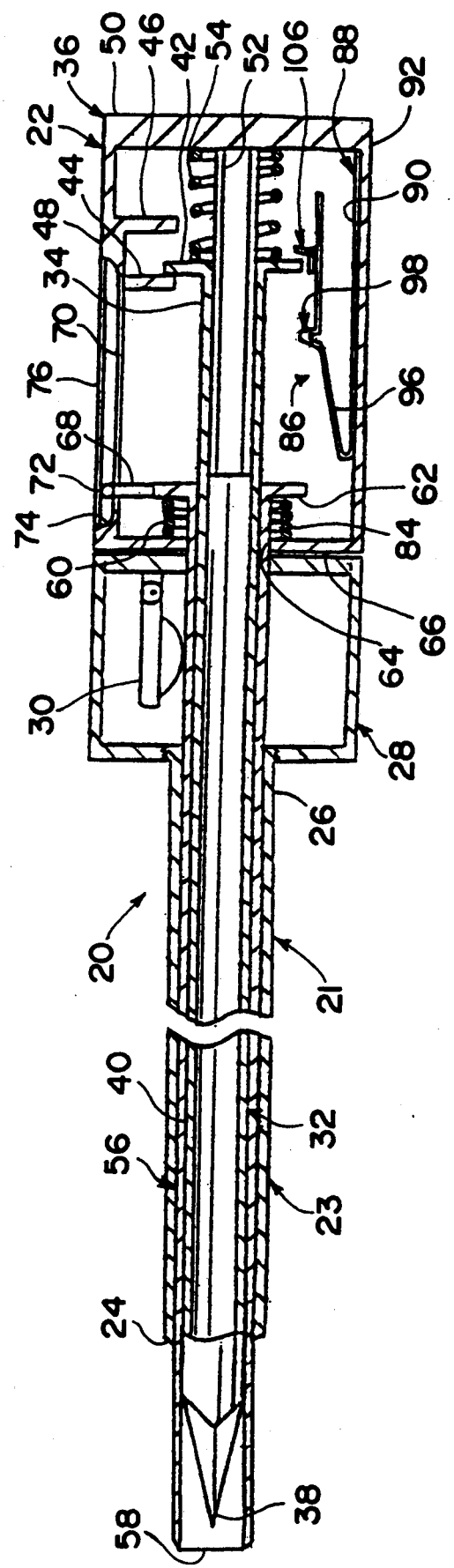
FIG. 1 is a broken longitudinal section of a safety penetrating instrument according to the present invention with the safety member in an extended, distally protruding position.
Figure 2:
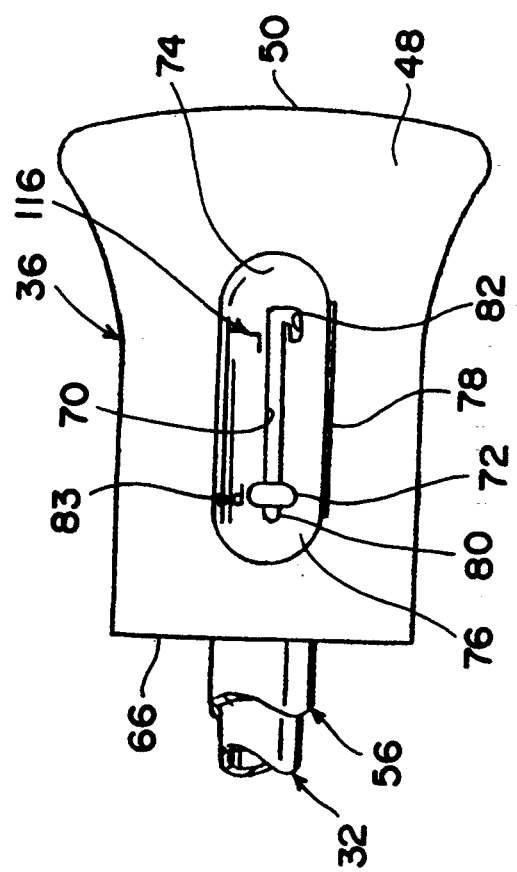
FIG. 2 is a top view of the hub of the safety penetrating instrument of FIG. 1.

A safety penetrating instrument 20 according to the present invention, as shown in FIGS. 1 and 2, is formed of a portal unit 21 and a penetrating unit 22. The portal unit 21 includes an elongate, cylindrical portal sleeve or cannula 23 having a distal end 24 and a proximal end 26 secured to a housing 28. The portal unit 21 is conventional and can be made of any desirable, medical grade materials dependent upon procedural use and desirability of being for single patient use or reusable. The housing 28 is preferably constructed to sealingly engage instruments passing therethrough and to include a valve 30 biased to a closed state when no instrument passes through the portal sleeve. A flapper valve 30 is shown; however, any suitable valve construction can be utilized, for example, trumpet or nipple valves.

The penetrating unit 22 includes an elongate penetrating member 32 having a proximal end 34 received in a hub 36, a sharp distal end or tip 38 and a shaft 40 extending between the proximal and distal ends. The distal end can have any configuration desired by a surgeon for a particular procedure, for example, the pyramidal trocar configuration shown or conical, threaded, multifaceted or open, slanted configurations. The penetrating member can be made of any suitable, medical grade materials and can be made of multiple components such that, for example, the distal tip 34 is made of stainless steel and secured in any conventional manner, such as by threads, to the distal end of shaft 40, which can be tubular and made of a less expensive material, such as plastic or metal. The proximal end 34 of penetrating member 32 is hollow and terminates at a transversely extending flange 42 positioned in hub 36 between spaced stops 44 and 46 depending from a top wall 48 of the hub. A rear wall 50 of the hub mounts a guide tube or rod 52 concentric with the longitudinal axis of the safety penetrating instrument 20 to be received in the open proximal end 34 of the penetrating member to allow the penetrating member to slide over the guide tube against the bias of a helical spring 54 coiled around guide tube 52 and mounted in compression between flange 42 and hub rear wall 50. A safety member or shield 56 has an elongate cylindrical configuration between a blunt distal end 58 and a proximal end 60 received in hub 36 and carrying a transversely extending flange 62. The safety shield can be made of any suitable, medical grade materials, such as plastic, can be made of multiple components and can have any desired configuration in cross section, preferably corresponding to the cross sectional configuration of the penetrating member. The blunt distal end 58 can have various configurations to protect tissue within an anatomical cavity by covering or shielding the distal tip of the penetrating member, for example, the configurations used on the Endopath and Surgiport trocars and the configurations disclosed in above mentioned U.S. patent application Ser. No. 07/817,113. The penetrating member 32 is concentrically received in the safety shield 56, and the penetrating member and safety shield slidably pass through an opening 64 in a front wall 66 of hub 36.

A pin 68 extends from flange 62 on the safety shield through a slot 70 in the top wall 48 of the hub to terminate at a handle 72 positioned in an elongate trough-like recess 74 in the top wall 48. A transparent cover 76 is pivotally mounted on top wall 48 via a hinge 78 to cover recess 74 and allow handle 72 to slide thereunder. As shown in FIG. 2, slot 70 and recess 74 extend longitudinally in parallel with the longitudinal axis of the safety penetrating instrument, and the slot 70 has a distal end 80 and terminates proximally at a transversely extending J-shaped portion to define a locking proximal slot end 82. A helical spring 84 is coiled around the proximal end 60 of the safety shield and mounted in tension with the ends of the spring 84 fixed to hub front wall 66 and safety shield flange 62. Spring 84 biases safety shield 56 distally toward an extended position where blunt distal end 58 protrudes beyond the sharp distal end 38 of penetrating member 32 and handle 72 is adjacent the distal end 80 of slot 70 in alignment with indicia "P" 83 as shown in FIGS. 1 and 2.

Figure 3:
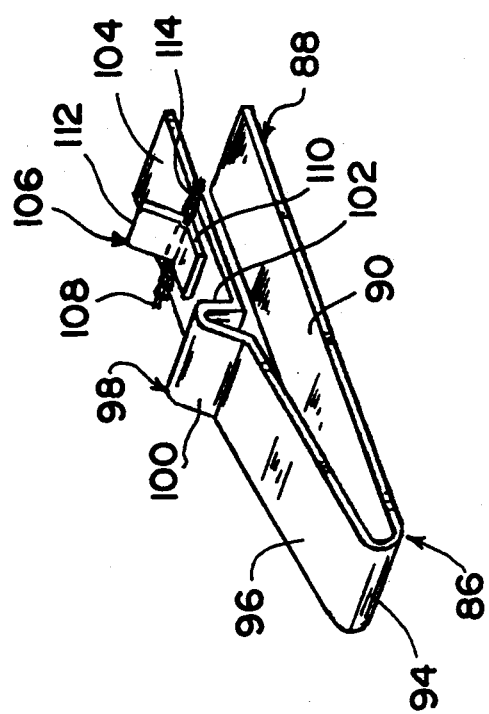
FIG. 3 is a perspective view of a locking and releasing mechanism for the safety penetrating instrument of FIG. 1.

A locking and releasing mechanism 86 for locking the safety shield in a retracted position exposing the sharp distal end 38 of the penetrating member and releasing the safety shield to allow the safety shield to return to the extended position, as shown in FIGS. 1 and 3, includes a latch or locking spring 88, made of a strip of resilient material formed to have a substantially flat base 90 secured to a bottom wall 92 of hub 36 and a bend 94 joining the base 90 with an upwardly angled arm 96 spaced from the base. Arm 96 carries a protruding latch 98 having a distal angled surface 100 joining a proximal latching surface 102 disposed substantially transversely to the longitudinal axis of the safety penetrating instrument and substantially parallel to the safety shield flange 62. Arm 96 has an extension 104 positioned proximally of latch 98, and a releasing member or trigger 106 is juxtaposed with extension 104. The trigger 106 is pivotally mounted in the hub on a pin 108 secured to a wall or walls of the hub or a structure supported in the hub, and the trigger is generally L-shaped with a leg 110 overlying extension 104 and a leg 112 extending substantially transversely from leg 110 but at a slight angle toward the proximal end of the safety penetrating instrument. A torsion spring 114 is coiled around pin 108 and fixed to trigger 106 to bias the trigger counterclockwise, looking at FIGS. 1 and 3, such that leg 110 is biased toward extension 104.

The portal unit 21 and the penetrating unit 22 can be provided to a surgeon separately or assembled together as shown in FIG. 1., and either or both of the portal and penetrating units can be manufactured in a manner to be disposable for single patient use or to be sterilizable for reuse. The hub 36 can be coupled to the housing 28 by suitable detent or latch mechanisms if desired.

Figure 4:
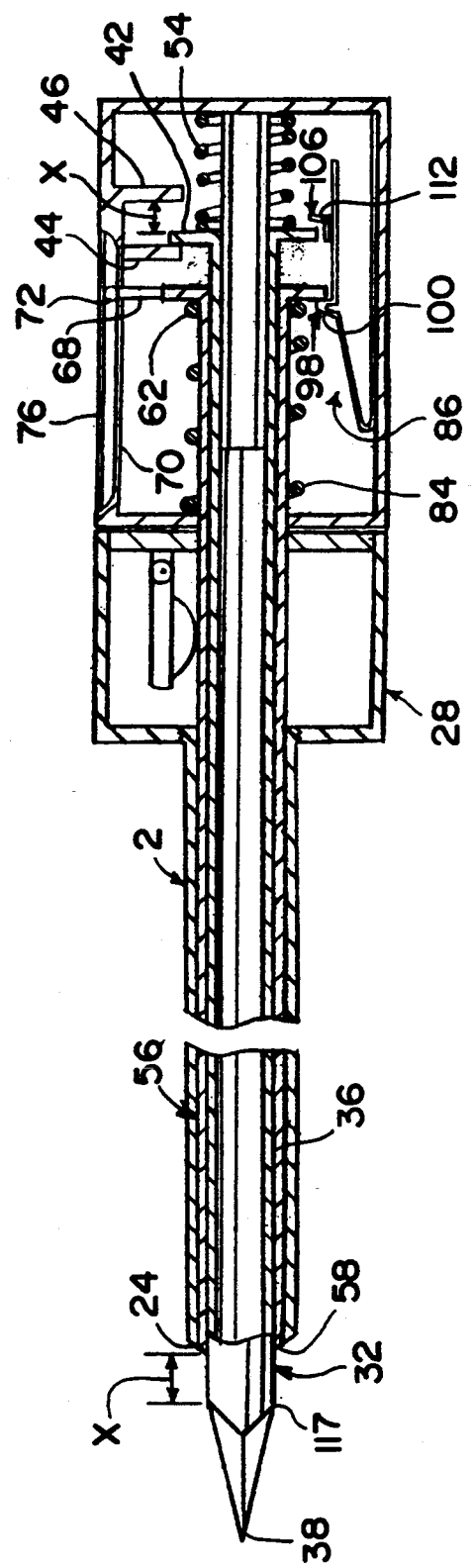
FIG. 4 is a broken longitudinal section of the safety penetrating instrument of FIG. 1 with the safety member in a locked retracted position.

In use, when a surgeon desires to penetrate into an anatomical cavity using the safety penetrating instrument 20, the instrument is in the condition shown in FIG. 1 with the safety shield 56 in the extended position to cover sharp distal tip 38 of the penetrating member. Prior to commencing penetration of an anatomical wall W, cover 76 is pivoted out of the way with a finger, and handle 72 is grasped and manually moved proximally to move safety shield 56 proximally against the bias of spring 84 until flange 62 rides over latch 98 by engaging angled distal surface 100 to move arm 96 toward base 90. At this time, the surgeon can feel the flange 62 lock into place in engagement with latching surface 102 as arm 96 springs back and can also visually determine that the safety shield is in the locked retracted position by noting the position of handle 72 in alignment with indicia "L" 116 disposed adjacent slot 70. The safety penetrating instrument 20 is now in the position illustrated in FIG. 4 with the safety shield 56 locked in the retracted position by locking and releasing mechanism 86 and the penetrating member 32 extending from the distal end 24 of the sleeve 23 and the distal end 58 of the safety shield 56, the distal ends 24 and 58 being in substantial alignment. The sharp distal end 38 of the penetrating member tapers to a sharp tip from a junction 117 with the shaft 36, and the distance X between junction 116 and the distal ends 24 and 58 of the sleeve and safety shield, respectively, is substantially the same as the distance X between the flange 42 on the proximal end of the penetrating member and the stop 46. The penetrating member is held in the extended position by the force from spring 54 which holds flange 42 against stop 44. In the position shown in FIG. 4, flange 42 is disposed distally of leg 112 of trigger 106.

Figure 5:
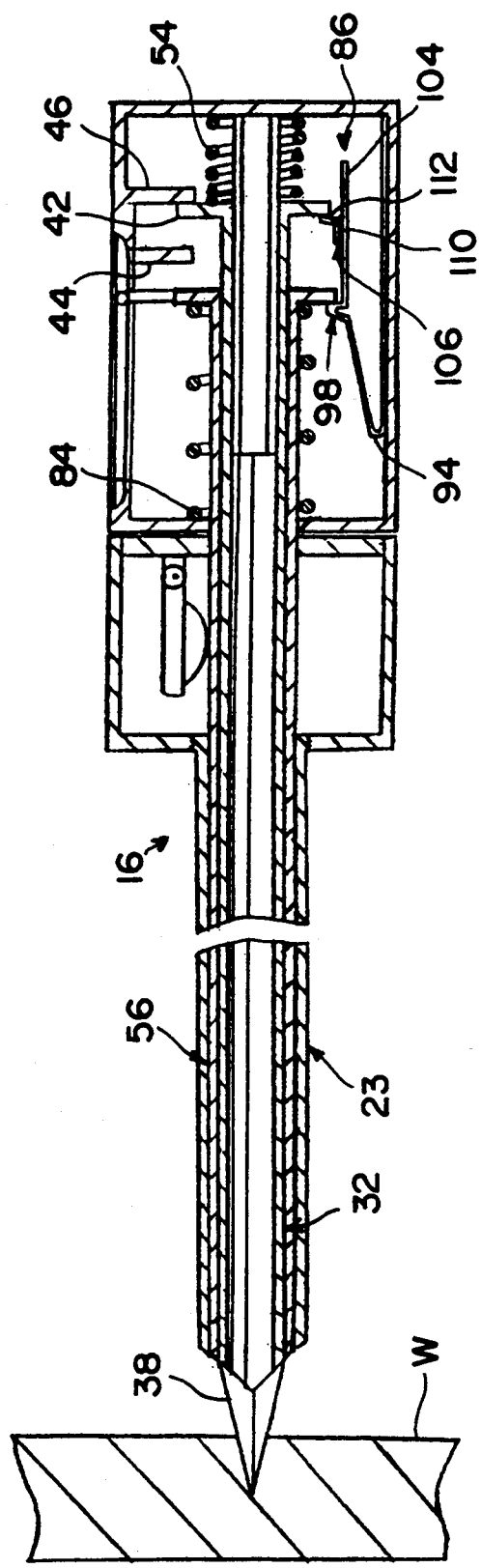
FIG. 5 is a broken longitudinal section of the safety penetrating instrument of FIG. 1 with the penetrating member moved proximally during penetration of an anatomical cavity wall.
Figure 6:
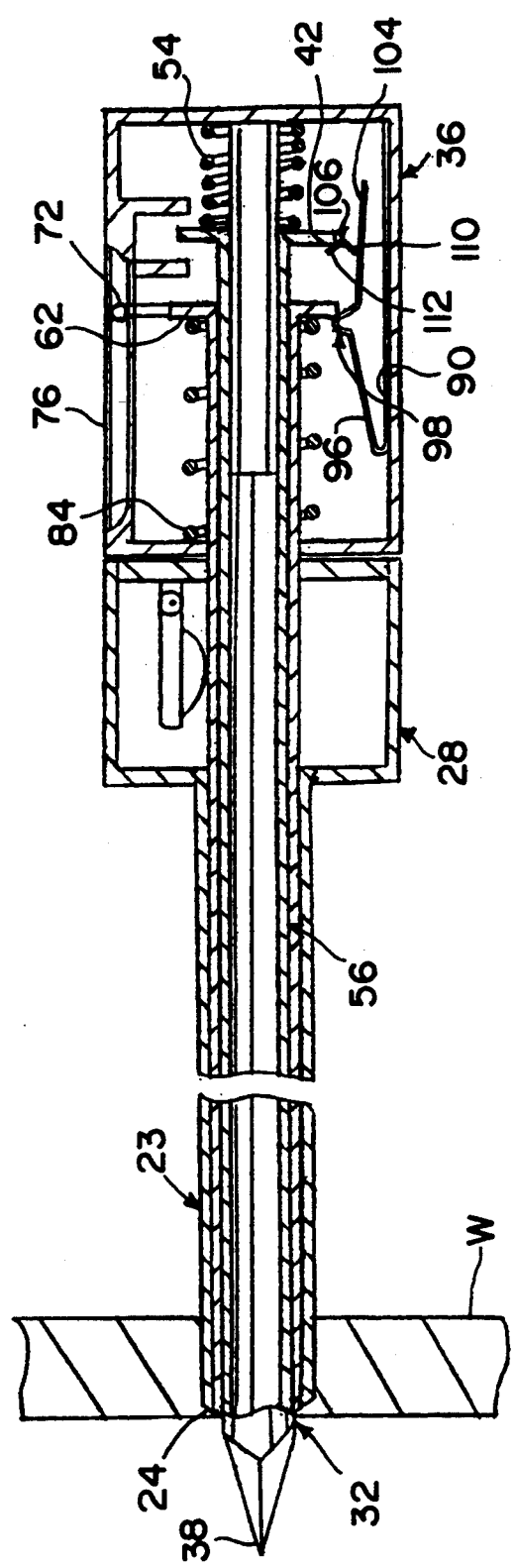
FIG. 6 is a broken longitudinal section of the safety penetrating instrument of FIG. 1 with the penetrating member moved distally to release the safety member.
Figure 7:
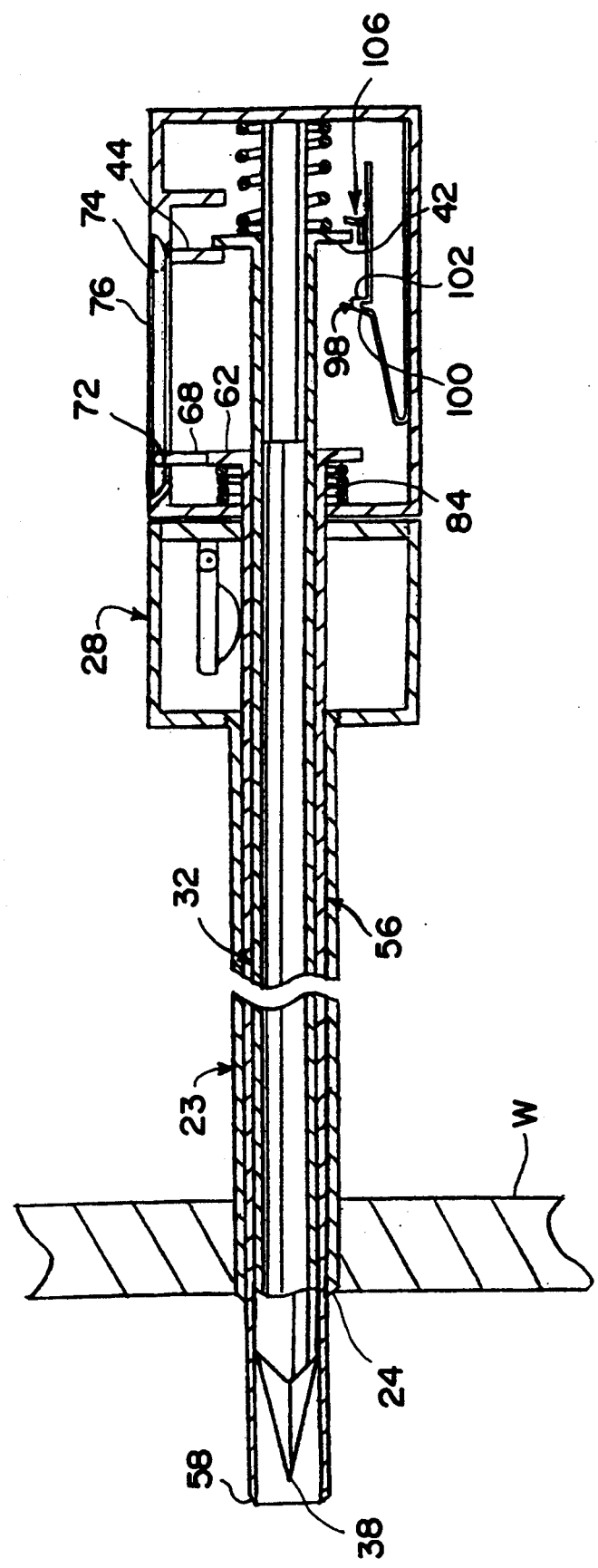
FIG. 7 is a broken longitudinal section of the safety penetrating instrument of FIG. 1 with the safety member in the extended position after penetrating into an anatomical cavity.

When the sharp distal end 38 of the penetrating member is brought into contact with an anatomical cavity wall W, the penetrating member 32 moves proximally against the bias of spring 54 until flange 42 abuts stop 46 as shown in FIG. 5. The flange 42 forms an operating member cooperating with the locking and releasing mechanism 86; and, as the flange 42 moves proximally, the operating member formed thereby engages leg 112 to pivot trigger 106 clockwise, looking at FIG. 5, to allow the operating member to pass thereby. The clockwise pivotal movement of trigger 106 does not cause movement of the latch 98 since there is no engagement by either leg 110 or 112 with arm extension 104; and, once the operating member passes by leg 112, spring 114 returns trigger 106 to its normal position with leg 110 adjacent arm extension 104. Accordingly, as penetration of the anatomical cavity wall W is commenced, the force to penetrate is limited to the force required to cause sharp distal end 38 to pass through the cavity wall W since the safety shield is held in the retracted position by engagement of flange 62 with latch 98. That is, during penetration, no force is required to overcome the bias of spring 84. As penetration continues, the safety penetrating instrument will advance through the cavity wall W to the position shown in FIG. 6 wherein the penetrating member 32 has passed entirely through the anatomical cavity wall and begins to move distally under the force of spring 54. As the penetrating member moves distally, the operating member formed by flange 42 engages leg 112 of trigger 106 causing the trigger to pivot counterclockwise looking at FIG. 6 and causing leg 110 to engage extension 104 moving arm 96 toward base 90 against the force of spring strip 88. The movement of arm 96 away from the longitudinal axis of the safety penetrating instrument causes latch 98 to move out of engagement with flange 62 on the safety shield thereby allowing spring 84 to move the safety shield distally to the extended position where distal end 58 protrudes beyond the sharp distal tip 38 of the penetrating member as illustrated in FIG. 7 thereby protecting tissue within the anatomical cavity from inadvertent contact with the sharp distal tip 38. With the distal end 58 of sleeve 23 in the anatomical cavity, the penetrating unit 22 can be withdrawn from the portal unit 21 leaving the sleeve in place such that instruments for performing endoscopic procedures can be introduced into the cavity via the portal formed by the portal unit.

By forming spring 84 to be relatively strong, protrusion of the safety shield 56 is assured even should the safety shield engage tissue in the anatomical cavity wall or within the anatomical cavity or should any tissue be jammed between the safety shield and the penetrating member or between the safety shield and the sleeve 23. Additionally, the strong force of spring 84 provides the surgeon with the psychological benefit of knowing the safety shield is protecting the penetrating member. Should tissue within the anatomical cavity be contacted by the distal end 58 of the safety shield, the safety shield can bounce or give a little in the manner of a shock absorber to protect such contacted tissue. Additionally, movement of the safety shield can be seen by the surgeon by noticing movement of handle 72 away from indicia 83 through the transparent cover 76. The strong force of spring 84 also provides the surgeon with an easily felt tactile signal that the safety shield has moved to the extended position and that penetration into the cavity has occurred which also can be visually confirmed by the position of handle 72 in slot 70.

Figure 8:
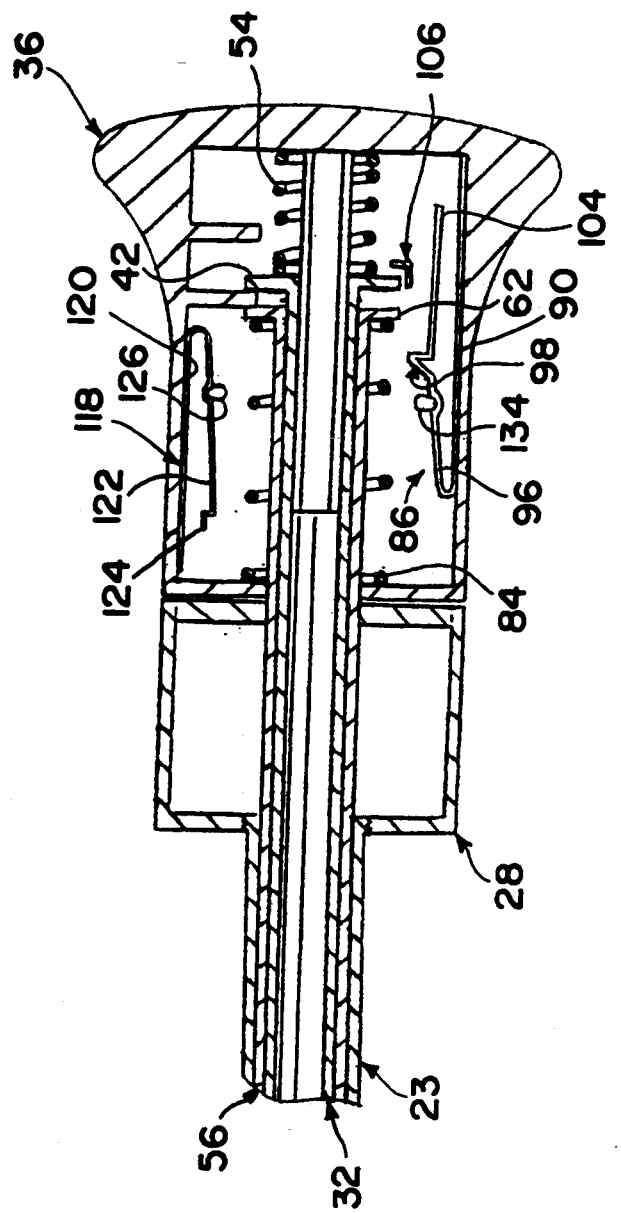
FIG. 8 is a broken longitudinal section of a modification of the safety penetrating instrument of the present invention.
Figure 9:
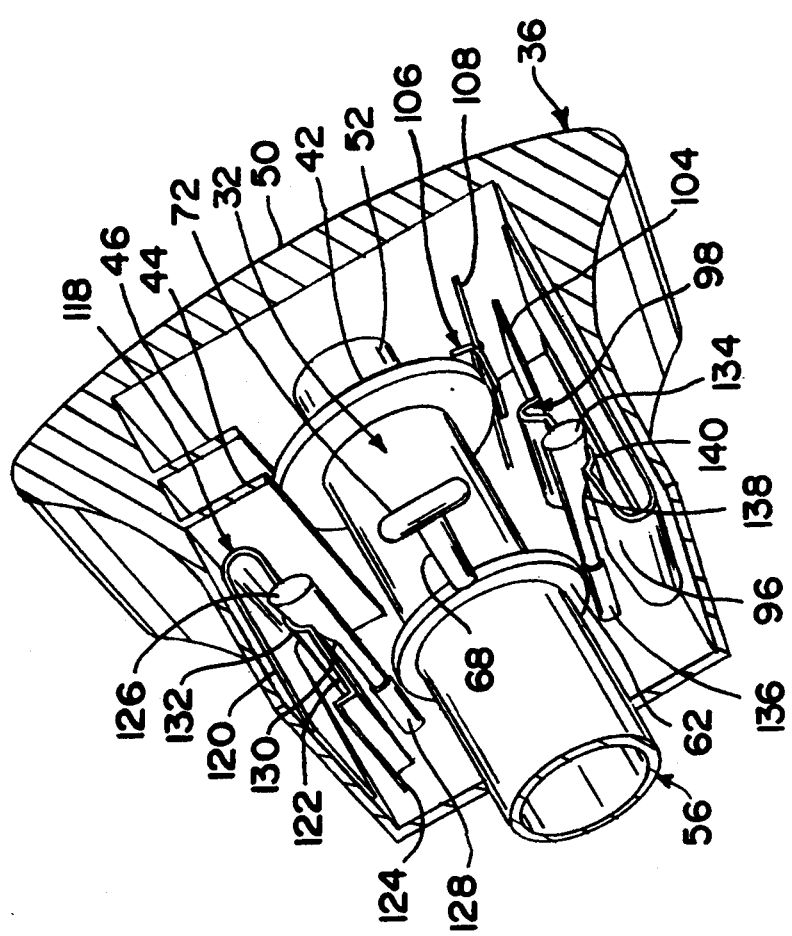
FIG. 9 is a broken perspective, partly in section, of the modification of FIG. 8.
Figure 10:
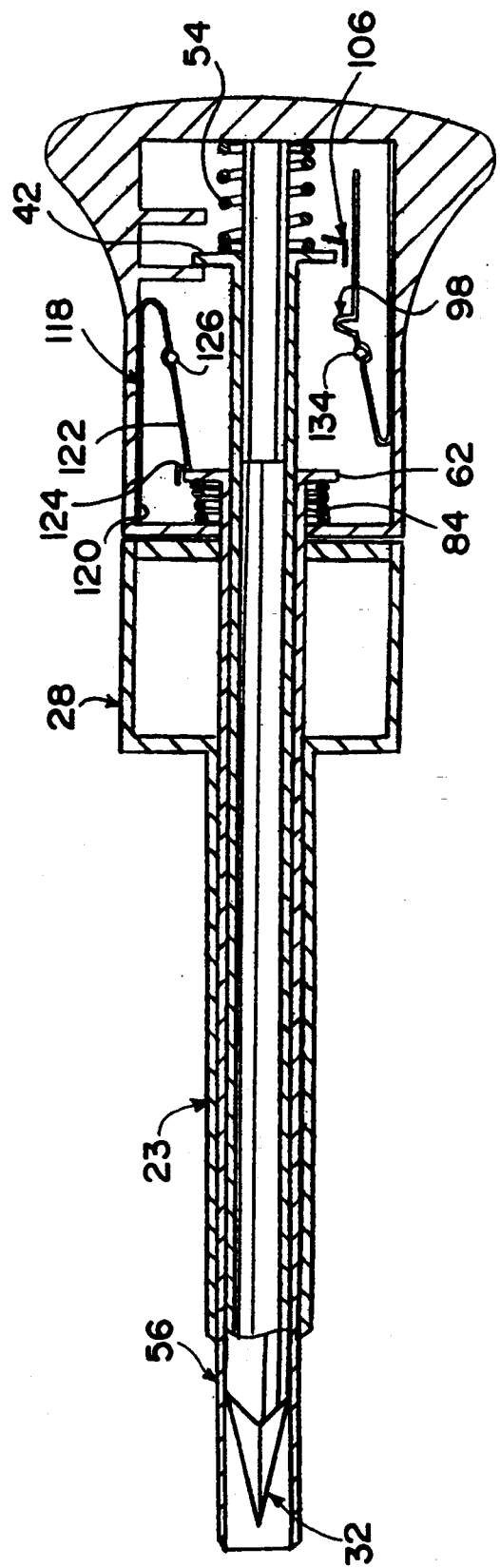
FIG. 10 is a broken longitudinal section of a safety penetrating instrument modified in accordance with FIG. 8 with the safety member in the extended position.

A modification of the safety penetrating instrument of the present invention is shown in FIGS. 8, 9 and 10 and further includes a locking mechanism 118 for locking the safety shield in the extended position. The locking mechanism 118 includes a spring made of a strip of resilient material having a base 120 secured to a sidewall of hub 36 and bending on itself to form a locking arm 122 spaced from base 120 and terminating at an offset locking finger 124. As shown in FIG. 10, the locking arm 122 is normally in a position such that locking finger 124 engages flange 62 on the proximal end of the safety shield 56; and, in order to allow movement of the safety shield proximally, a control button 126 is mounted in the hub and has a small diameter end received in a socket 128 extending from the bottom wall of the hub. The end of control button 126 protrudes from the top wall of the hub to allow longitudinal movement of the control button, and the control button includes a tapered portion 130 contacting a groove or recess 132 in the locking arm 122. In this manner, depressing the control button 126 moves the locking arm out of the locking position shown in FIG. 10 to the disabled position illustrated in FIG. 8. Accordingly, the locking mechanism can be utilized to permit automatic or selective locking of the safety shield in the extended position, if desired, by movement of control button 126.

Additionally, the modification shown in FIGS. 8, 9 and 10 includes a control button 134 having a small diameter portion mounted in a socket 136 and a tapered portion 138 received in a groove or recess 140 in arm 96 of locking and releasing mechanism 86. The control button 134 can be utilized to disable the latching operation produced by locking and releasing mechanism 86 in that, by depressing control button 134, arm 96 can be moved away from the longitudinal axis of the safety penetrating instrument to prevent latch 98 from engaging flange 62 on the proximal end of the safety shield. Accordingly, with the control button 134 depressed, the safety penetrating instrument can operate like a standard safety shielded trocar.

Use of the control button 126 allows the surgeon to selectively control the safety penetrating instrument to produce automatic locking of the safety shield upon penetration into the anatomical cavity since, with control button 126 extended or not depressed, flange 62 of the safety shield will flex arm 122 toward base 120 as the safety shield moves distally until flange 62 passes locking finger 124 at which time the locking finger will spring back to engage the flange and prevent proximal movement of the safety shield as shown in FIG. 10. To allow the safety shield to be proximally moved either prior to penetration or after penetration, the surgeon depresses control button 126 to cause tapered portion 130 to engage groove 132 and flex arm 122 to the position shown in FIG. 8 such that the locking finger is moved out of the path of safety shield flange 62. In a similar fashion, control button 134 allows the surgeon to selectively control operation of the locking and releasing mechanism 86 since depression of the control button 134 will cause tapered portion 138 to engage groove 140 and flex arm 96 toward base 90 moving latch 98 out of the path of safety shield flange 62 and extension 104 away from trigger 106. Accordingly, proximal movement of the safety shield cannot move flange 62 to a position where the flange engages latch 98; and, thus, the safety shield is free to move proximally and distally similar to a conventional safety shielded trocar.

Accordingly, the safety penetrating instrument can be used with the safety shield triggered by the operating member when the control button 134 is not depressed or with the safety shield free to move like a standard safety shielded trocar. Additionally, handle 72 can be moved to lock pin 68 in J-shaped proximal slot portion 82 such that the safety penetrating instrument can be used as a standard trocar since the safety shield is not free to move or to be triggered. Thus, with a single instrument, the surgeon has various options to be selected in accordance with particular procedures to be performed or particular surrounding circumstances.

Figure 11:
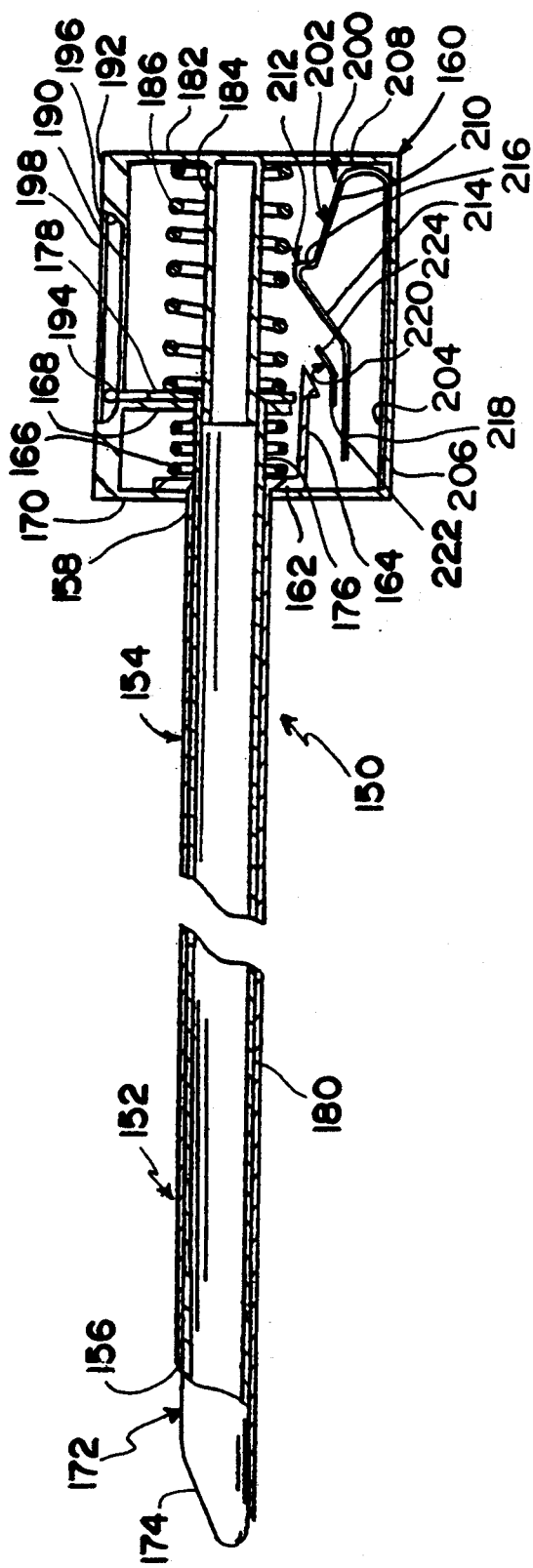
FIG. 11 is a broken longitudinal section of another embodiment of a safety penetrating instrument according to the present invention with the safety member in the extended position.

Another embodiment of a safety penetrating instrument 150 according to the present invention is shown in FIG. 11 with the portal unit not illustrated in that the portal unit can be the same as portal unit 21. The primary difference between safety penetrating instruments 20 and 150 is that the positions of the penetrating member and the safety member are reversed in that the penetrating member is hollow and the safety member is disposed within the penetrating member. Safety penetrating instrument 150 includes a penetrating unit 15.2 having a cannulated, elongate, hollow, tubular penetrating member 154 terminating at an angled, open, sharp distal end 156 and at a proximal end 158 received in a hub 160. The proximal end 158 carries a flange 162, and an operating member 164 with a barbed end extends proximally from flange 162 in parallel with the longitudinal axis of the safety penetrating instrument. The penetrating member 154 is biased distally by a helical spring 166 mounted in compression between a wall 168 in the hub 160 and the flange 162 such that flange 162 is biased to abut a front wall 170 of the hub.

A safety member in the form of an elongate, tubular or solid probe 172 is slidably disposed in penetrating member 154 and has a blunt distal end 174 disposed at an angle to the longitudinal axis of penetrating member 154 substantially the same as the angle of penetrating member distal end 156. The safety probe 172 has a hollow proximal end 176 terminating at a transversely extending flange 178, and the distal and proximal ends of the safety probe can be connected via any suitable member such as a tubular shaft 180. A rear wall 182 of the hub mounts a guide tube or rod 184 concentric with the longitudinal axis of the safety penetrating instrument 150 to be received in the open proximal end 176 of the safety probe 172 to allow the safety probe to slide over the guide tube against the bias of a helical spring 186 coiled around guide tube 184 and mounted in compression between flange 178 and hub rear wall 182. The safety probe can be made of any suitable, medical grade materials, such as plastic, and have any desired configuration in cross-section; however, it is preferred that the blunt distal end 174 have a configuration corresponding to the configuration of the open distal end 156 of the penetrating member 154 as disclosed in above-mentioned patent application Ser. No. 07/628,899. The configuration of the blunt distal end 154 is preferably smooth to protect tissue within an anatomical cavity from contact therewith and further to cover or protect the sharp distal tip 156 of the penetrating member.

A pin 188 extends from flange 178 on the safety probe through a slot 190 in a top wall 192 of the hub to terminate at a handle 194 positioned in an elongate recess or trough 196 in the top wall, the slot and trough having the configuration illustrated in FIG. 2 and similarly having a transparent cover 198 pivotally mounted thereover.

A locking and releasing mechanism 200 for locking the safety probe in a retracted position exposing the sharp distal tip 156 of the penetrating member and releasing the safety probe to allow the safety probe to return to the extended position includes a latch or locking spring 202 made of a strip of resilient material formed to have a substantially flat base 204 secured to a bottom 206 of hub 160 and a bend 208 joining the base 204 with an upwardly angled arm 210 spaced from the base. Arm 210 carries a protruding latch 212 having a distal angled surface 214 joining a proximal latching surface 216 disposed substantially transversely to the longitudinal axis of the safety penetrating instrument and substantially parallel to the safety probe flange 178. Arm 210 has a distally extending extension 218, and a releasing member or trigger 220 is juxtaposed with extension 218. The trigger 220 is pivotally mounted in the hub on a pin in the manner described above with respect to trigger 106 and is similarly spring biased in a counterclockwise direction looking at FIG. 11. Similarly, trigger 220 has a generally L-shaped configuration with a leg 222 overlying extension 218 and a leg 224 extending transversely or at an angle toward the proximal end of the safety penetrating instrument.

Figure 12:
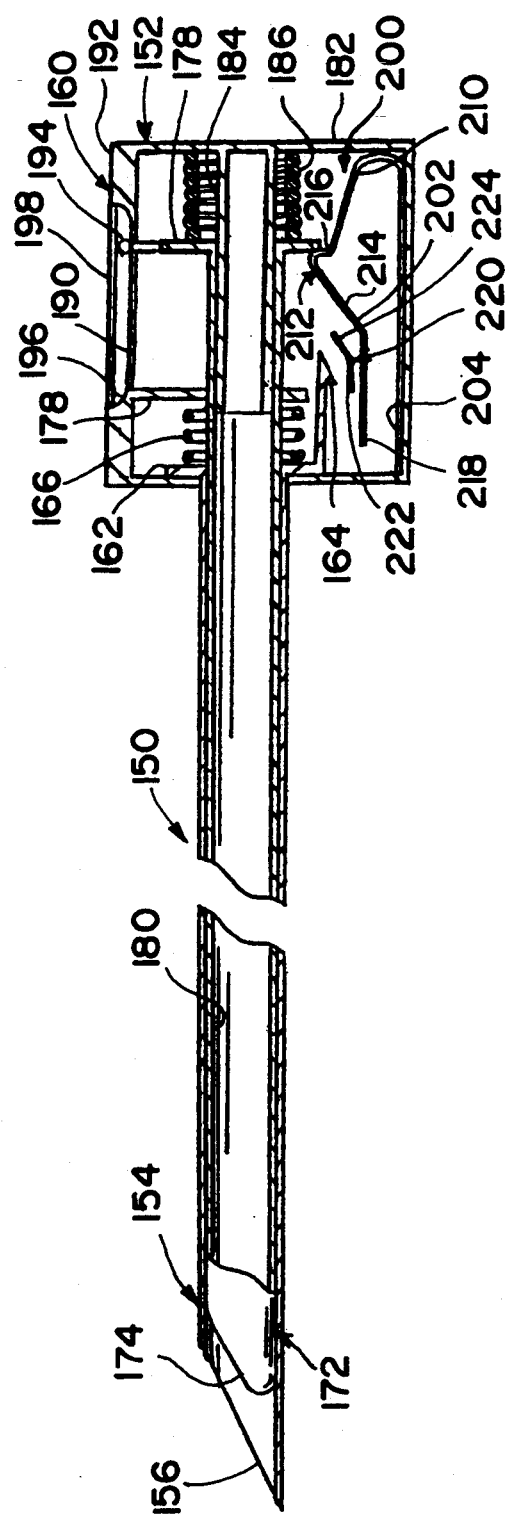
FIG. 12 is a broken longitudinal section of the safety penetrating instrument of FIG. 11 with the safety member in the locked retracted position.
Figure 13:
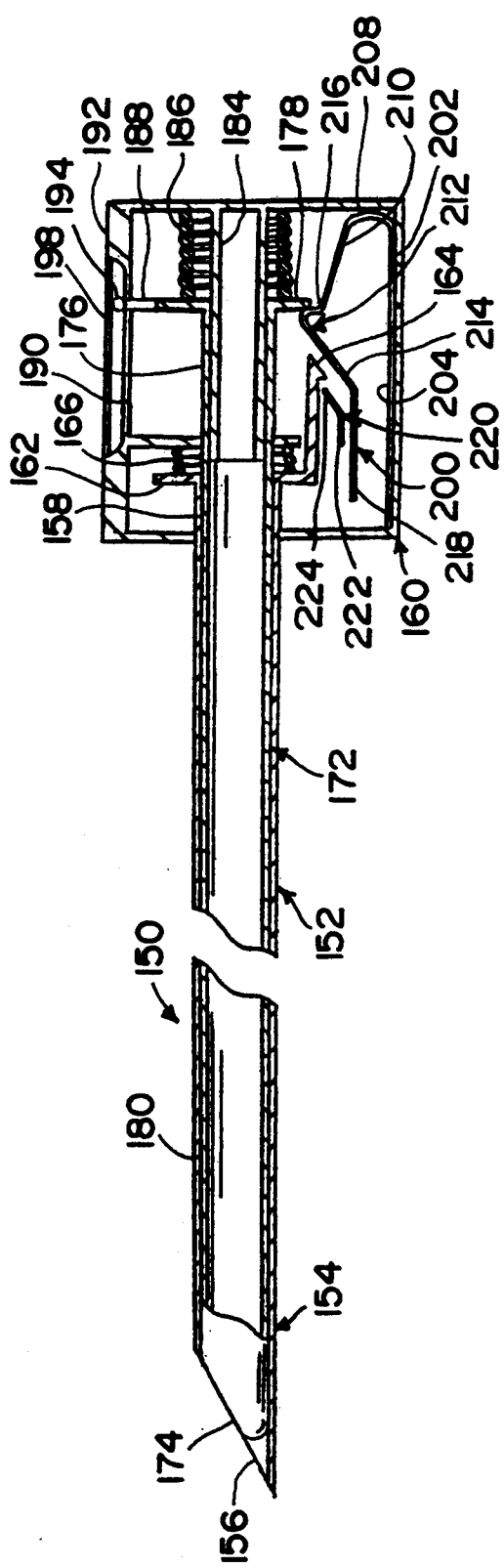
FIG. 13 is a broken longitudinal section of the safety penetrating instrument of FIG. 11 with the penetrating member moved proximally during penetration of an anatomical cavity wall.

Use of the safety penetrating instrument 150 is similar to that described above with respect to safety penetrating instrument 16 in that, when a surgeon desires to penetrate into an anatomical cavity, the safety penetrating instrument is in the condition shown in FIG. 11 with the safety probe 172 extended such that the safety probe distal end 174 protrudes beyond the penetrating member distal end 156. Prior to commencing penetration of an anatomical cavity wall, cover 198 is pivoted away from trough 196, and the safety probe is moved to the retracted position by grasping handle 194 and moving the knob proximally until the flange 178 rides over angled proximal surface 214 of the locking and releasing mechanism to be latched in the retracted position by engagement with latch 212 as shown in FIG. 12. As previously noted, the surgeon can feel the flange lock into place in engagement with the latching surface and can also visually determine that the safety probe is in the locked retracted position by noting the position of the handle 194 in alignment with indicia disposed adjacent the slot 190. With the safety penetrating instrument 150 in the position illustrated in FIG. 12, penetration of the cavity wall is commenced, and the force on the distal end 156 of the penetrating member will cause the penetrating member to move proximally against the bias of spring 166 to the position illustrated in FIG. 13 wherein the distal end 174 of the safety probe is aligned with the distal end of the penetrating member. Additionally, the operating member barb 164 will move past trigger 220 causing the trigger to rotate in a clockwise direction so as not to cause movement of the latch. Accordingly, the barb 164 is now positioned proximally of the trigger 220. Upon entry into the anatomical cavity, the counter force on the distal end of the penetrating member will be reduced allowing spring 166 to move the penetrating member distally causing operating member 164 to engage leg 224 of trigger 220 and pivot the trigger counterclockwise causing leg 222 to engage arm extension 218. The engagement of leg 222 with extension 218 causes arm 210 to move toward base 204 moving the latch 212 out of engagement with flange 178 thereby allowing spring 186 to cause the safety probe to move distally to the position shown in FIG. 11 wherein safety probe distal end 174 protrudes beyond the distal end 156 of the penetrating member.

Figure 14:
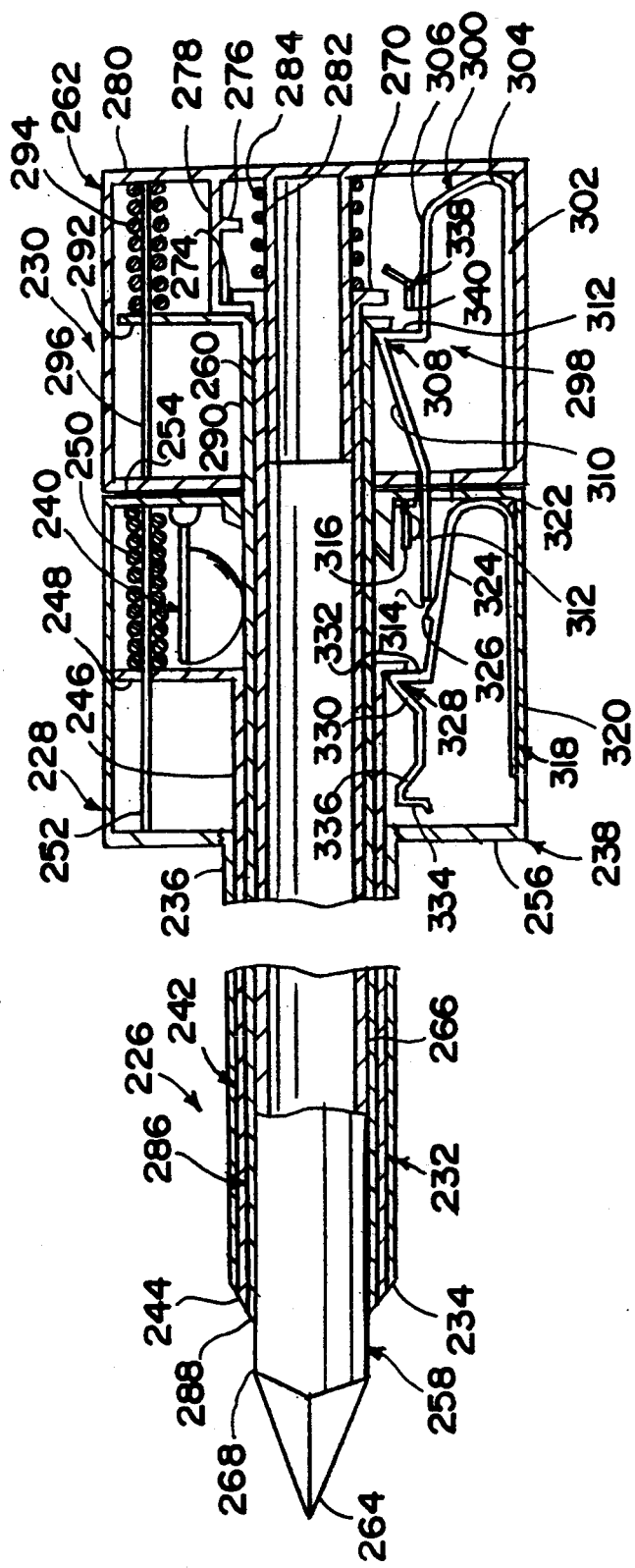
FIG. 14 is a broken longitudinal section of another embodiment of a safety penetrating instrument according to the present invention.

Another embodiment of a safety penetrating instrument 226 according to the present invention is shown in FIG. 14 with the primary difference between safety penetrating instruments 20 and 26 being that the safety member or shield is mounted in the portal unit housing to be left in place in the portal sleeve after the penetrating unit is withdrawn. Safety penetrating instrument 226 includes a portal unit 228 and a penetrating unit 230. The portal unit 228 includes an elongate cylindrical portal sleeve or cannula 232 having a distal end 234 and a proximal end 236 secured to a housing 238 mounting a valve 240. A safety member in the form of a shield 242 has an elongate, cylindrical configuration between a blunt distal end 244 and a proximal end 246 received in housing 238 and carrying a transversely extending flange 248. The safety shield 242 has a configuration to fit within sleeve 232 in sliding engagement therewith, and a helical spring 250 is coiled around a guide rod 252 and mounted in compression between flange 248 on the proximal end of the safety shield and a rear wall 254 of housing 238 to bias safety shield 242 distally such that the safety shield is normally in an extended position with the distal end 244 extending beyond the penetrating member and the flange 248 is adjacent a front wall 256 of housing 238.

The penetrating unit 230 .includes an elongate penetrating member 258 having a proximal end 260 received in a hub 262, a sharp distal end or tip 264 and a shaft 266 extending between the proximal and distal ends. As shown, the distal end has facets tapering from a junction 268 to a sharp point as in a conventional three-sided trocar; however, the distal end 264 can have any desired configuration. The proximal end 260 of penetrating member 258 is hollow and terminates at a transversely extending flange 270 positioned in hub 262 between spaced stops 274 and 276 depending from a wall 278 extending from a rear wall 280 of the hub. The rear wall 280 mounts a guide tube or rod 282 concentric with the longitudinal axis of the safety penetrating instrument 226 to be received in the open proximal end 260 of the penetrating member to allow the penetrating member to slide over the guide tube against the bias of a helical spring 284 coiled around guide tube 282 and mounted in compression between flange 270 and hub rear wall 280. The penetrating unit 230 also includes a protective sheath 286 having a hollow tubular configuration and terminating at a distal end 288 adjacent sleeve distal end 234 and safety shield distal end 244 and at a proximal end 290 having a flange 292 extending transversely therefrom. The protective sheath 286 is biased distally by a helical spring 294 coiled around a guide rod 296 and mounted in compression between hub rear wall 280 and flange 292 on the proximal end of the protective sheath. The protective sheath 286 surrounds the penetrating member 258 and is in interior engagement with safety shield 242.

A locking and releasing mechanism 298 for locking the safety shield and the protective sheath in a retracted position exposing the sharp distal end 264 of the penetrating member and for releasing the safety shield and the protective sheath to allow the safety shield and the protective sheath to return to the extended position beyond the distal end 264 of the penetrating member 65 includes a latch or locking spring 300 made of a strip of resilient material formed to have a substantially flat base 302 secured to a bottom wall of hub 262 and a bend 304 joining the base 302 with an arm 306 spaced from the base. Arm 306 carries a protruding latch 308 having a distal angled surface 310 joining a proximal latching surface 312 disposed substantially transversely to the longitudinal axis of the safety penetrating instrument and substantially parallel to the protective sheath flange 292. Proximal latching surface 310 joins a distal arm extension 312 passing through aligned openings in the front wall of hub 262 and the rear wall of housing 238 to terminate at an end 314. A valve member 316 is mounted adjacent the opening in the rear wall of housing 238 to seal the opening therein closed when the extension 312 is withdrawn therefrom. The locking and releasing mechanism 298 also includes a latch or locking spring 318 made of a strip of resilient material formed to have a substantially flat base 320 secured to a bottom wall of housing 238 and a bend 322 joining the base 320 with an upwardly angled arm 324 spaced from the base. Arm 324 carries a bump 326 disposed adjacent the end 314 of extension 312 and, distally of bump 326, carries a protruding latch 328 having a distal angled surface 330 joining a proximal latching surface 332 disposed substantially transversely to the longitudinal axis of the safety penetrating instrument and substantially parallel to the safety shield flange 248. Angled surface 330 leads to a locking finger 334 via a distally angled surface 336. A trigger 338 is pivotally mounted in hub 262 and has the same general L-shape configuration as trigger 106 with a leg 340 overlying arm 306 and a leg 342 disposed in the path of movement of the operating member formed by flange 270 on the proximal end of the penetrating member 258.

In use, the safety penetrating instrument 226 will initially be in a position with safety shield 242 and protective sheath 286 extended beyond the sharp distal end 264 of the penetrating member such that flange 248 of the safety shield is adjacent the front wall 256 of housing 238 and flange 292 of the protective sheath is adjacent the front wall of hub 262. In order to move the safety shield and the protective sheath to the retracted positions shown in FIG. 14, a handle such as that shown in safety penetrating instrument 20 is grasped to move the safety shield and the protective sheath proximally while the locking finger 334 is depressed toward base 320 to allow movement of the safety shield, it being appreciated that locking finger 334 will lock the safety shield in the extended position when the locking finger is in the position shown in FIG. 14. A similar locking finger can be formed on extension 312 to lock the protective sheath in an extended position if desired. During penetration of a cavity wall, penetrating member 264 will move proximally until flange 270 engages stop 276 in which position junction 268 at the distal end of the penetrating member will be aligned with the distal ends of the safety shield and the protective sheath. In this position, in a manner similar to that described above with respect to safety penetrating instrument 20, the operating member 270 will have moved past the trigger 338 to be positioned just proximally of leg 342. Upon entry into the anatomical cavity, spring 284 will move penetrating member 258 distally causing the operating member formed by flange 270 to engage leg 342 pivoting the trigger 338 to cause leg 340 to engage arm 306 moving latch 308 out of engagement with flange 292 of the protective sheath and allowing spring 294 to move the protective sheath distally to the extended position. At the same time, the end 314 of extension 312 will be moved to engage bump 226 on arm 324 moving arm 324 toward base 320 and disengaging latch 328 allowing the safety shield 242 to be moved distally to the extended position by spring 250. As the safety shield moves distally, flange 248 will ride over the ramp formed by angled surface 336 allowing locking finger 334 to depress and then move into a locking position holding the safety shield in the extended position. As previously noted, the same automatic locking mechanism can be utilized for the protective sheath. Once penetration is complete, the penetrating unit is removed from the portal unit withdrawing the penetrating member 258 and the protective sheath 286 leaving the safety shield 242 in place within the sleeve 232 such that the safety shield assures communication with the anatomical cavity in the event that the sleeve 232 has not been received in the anatomical cavity. When the penetrating unit is withdrawn, the protective sheath 286 will be in the extended position shielding the sharp tip 264 of the penetrating member to prevent inadvertent contact by personnel in the operating room.

The primary use of the protective sheath 286 is to cover the sharp tip 264 of the penetrating member once the penetrating unit is withdrawn from the portal unit; and, accordingly, the protective sheath can be biased distally by a weak spring so as to add only a small resistance to penetration if the protective sheath is not locked in a retracted position during penetration. In this case, the protective sheath need not be released with no locking and releasing mechanism therefor required. Additionally, the protective sheath can be biased to be in the extended position only when the portal unit and the penetrating unit are not assembled such that the protective sheath moves to the retracted position upon assembly of the portal unit and the penetrating unit.

Figure 15:
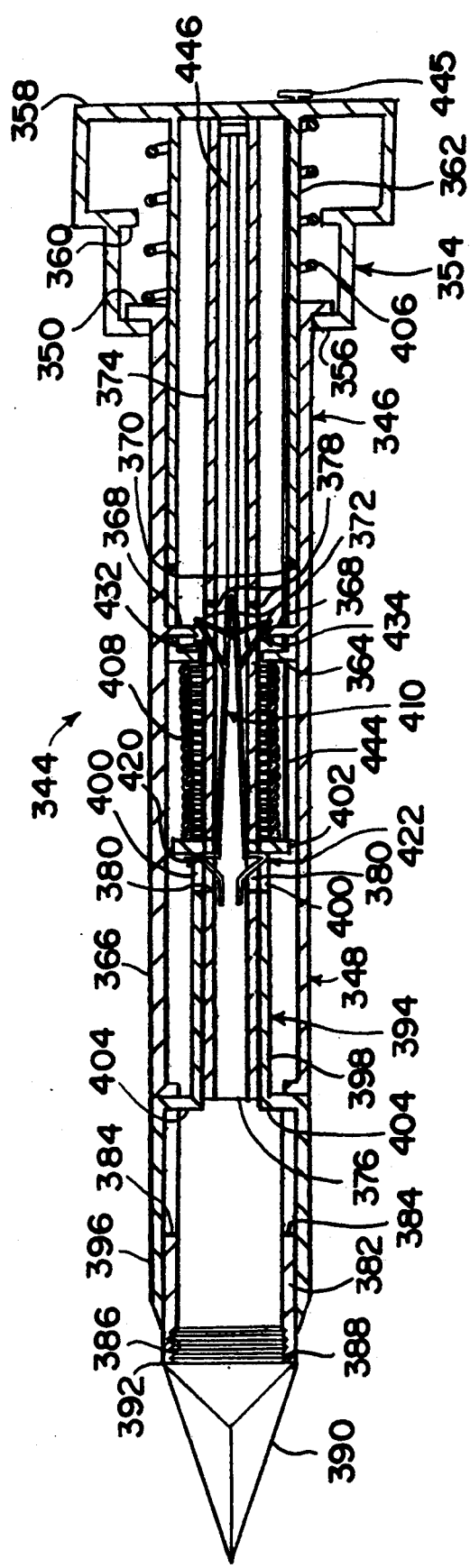
FIG. 15 is a longitudinal section of a further embodiment of a safety penetrating instrument according to the present invention.

A further embodiment of a safety penetrating instrument 344 according to the present invention is shown in FIG. 15 with the portal unit not illustrated in that the portal unit can be the same as portal unit 21. The primary difference between safety penetrating instruments 20 and 344 is that in the safety penetrating instrument 344 the locking and releasing mechanism is disposed within the penetrating member between the hub and the distal end. More particularly, safety penetrating instrument 344 includes a penetrating unit 346 formed of an elongate penetrating member 348 having a proximal end terminating at a flange 350 received in a hub 354. The hub 354 has a front wall 356, a rear wall 358, a stop 360 spaced from front wall 356, a guide tube 362 extending concentrically with the axis of the safety penetrating instrument from the rear wall 358 to a distal end wall 364 disposed within a hollow shaft 366 of the penetrating member such that the penetrating member slides on the guide tube 362. Operating members 368 extend radially inwardly from shaft 366 through slots 370 in guide tube 362 to terminate at beveled ends 372. A support tube 374 extends from hub rear wall 358 concentrically within guide tube 362 to terminate distally at an open end 376, and the support tube 374 has opposed slots 378 formed therein adjacent operating members 368 and opposed slots 380 spaced distally from slots 378. Penetrating member 348 has a smaller diameter neck 382 at the distal end of shaft 366 with slots 384 therein, and the end of neck 382 is internally threaded at 386 to receive external threads 388 on a sharp, tissue penetrating tip 390 having facets extending from a junction 392 to a sharp point. Various tips 390 having procedure specific configurations desired by a surgeon, such as conical, multifaceted or blunt, for example, can be secured to the distal end of the penetrating member by threading. A safety member 394 has a shield-like distal portion 396 and a narrow tubular neck 398 extending along support tube 374 with slots 400 therein adjacent a flange 402 at the proximal end of the safety member. The shield portion 396 is joined to neck 398 via spaced shoulders 404 passing through slots 384 in the penetrating member. A helical spring 406 is coiled around guide tube 362 and mounted in compression between flange 350 on the proximal end of the penetrating member and the rear wall of hub 354, and a helical spring 408 is coiled around support tube 374 and mounted in compression between distal end wall 364 of guide tube 362 and flange 402 on the proximal end of the safety member. Accordingly, spring 406 biases the penetrating member distally, and spring 408 biases the safety member distally.

Figure 16:
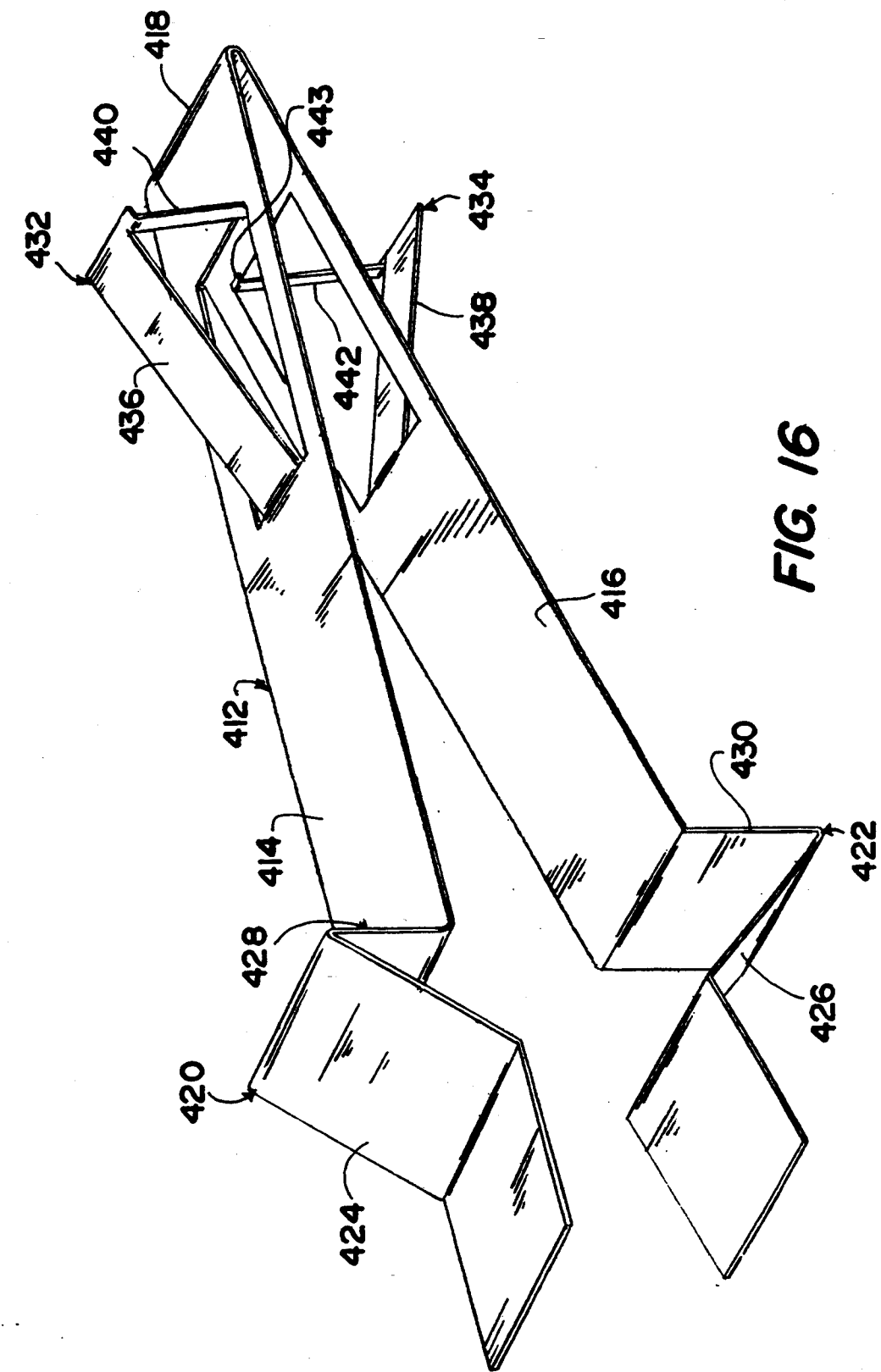
FIG. 16 is a perspective view of the locking and releasing mechanism of the safety penetrating instrument of FIG. 15.

A locking and releasing mechanism 410 for locking the safety member in a retracted position exposing the sharp distal end 390 of the penetrating member and releasing the safety member to allow the safety member to return to the extended position includes, as shown in FIGS. 15 and 16, includes a latch or locking spring 412 having spaced, angled arms 414 and 416 extending from a bend 418 and carrying protruding latches 420 and 422 formed of distal angled surfaces 424 and 426 joining proximal latching surfaces 428 and 430, respectively, the latching surfaces being disposed substantially transversely to the longitudinal axis of the safety penetrating instrument and substantially parallel to the safety member flange 402. Arms 412 and 416 are each cut away to form triggers 432 and 434, respectively, formed of angled arms 436 and 438 bent from arms 412 and 414, respectively, and legs 440 and 442 extending from the free ends of arms 336 and 338, respectively, to terminate at lips 443 engaging the underside of the respective arms.

In use, the safety member 394 is normally in an extended position such that shield portion 396 extends beyond the sharp tip 390 of the penetrating member with shoulders 404 at the distal ends of slots 384 in the penetrating member. With the safety shield biased to the extended position by spring 408, flange 402 is positioned adjacent the junction of neck 382 and shaft 366 of the penetrating member distally of latches 420 and 422. When it is desired to penetrate an anatomical cavity wall, the safety member is moved proximally by means of a rod 444 attached to flange 402 and extending along support tube 374 through hub rear wall 358 to a handle 445 to permit the safety member to be moved proximally against the bias of spring 408 causing flange 402 to ride over angled surfaces 424 and 426 and be locked in the retracted position by latching surfaces 428 and 430. The latch or locking spring 412 is mounted on a rod 446 extending from hub rear wall 358 within support tube 374 at a position such that triggers 432 and 434 extend through slots 378 while latches 420 and 422 extend through slots 380 in the support tube 374 and slots 400 in the safety member 394. Once the safety member is in the locked retracted position, penetration of the anatomical cavity wall can be accomplished with the force on the distal tip of the penetrating member moving the penetrating member proximally against the bias of spring 406 to a position limited by abutment with stop wall 360 in hub 354. As the penetrating member moves proximally, beveled ends 372 of operating members 368 move past arms 436 and 438 causing the triggers 432 and 434 to depress without moving the latches 420 and 422 which are biased away from each other by latch or locking spring 412. Accordingly, as the anatomical cavity wall is penetrated, the operating members 368 are positioned proximally of triggers 432 and 434; and, once penetration into the anatomical cavity is accomplished, spring 406 will move the penetrating member distally causing operating members 368 to engage triggers 432 and 434 moving legs 436 and 438 distally and causing arms 414 and 416 to flex toward each other to disengage latches 420 and 422 from flange 402 allowing spring 408 to move the safety member distally to the extended position.

Figure 17:
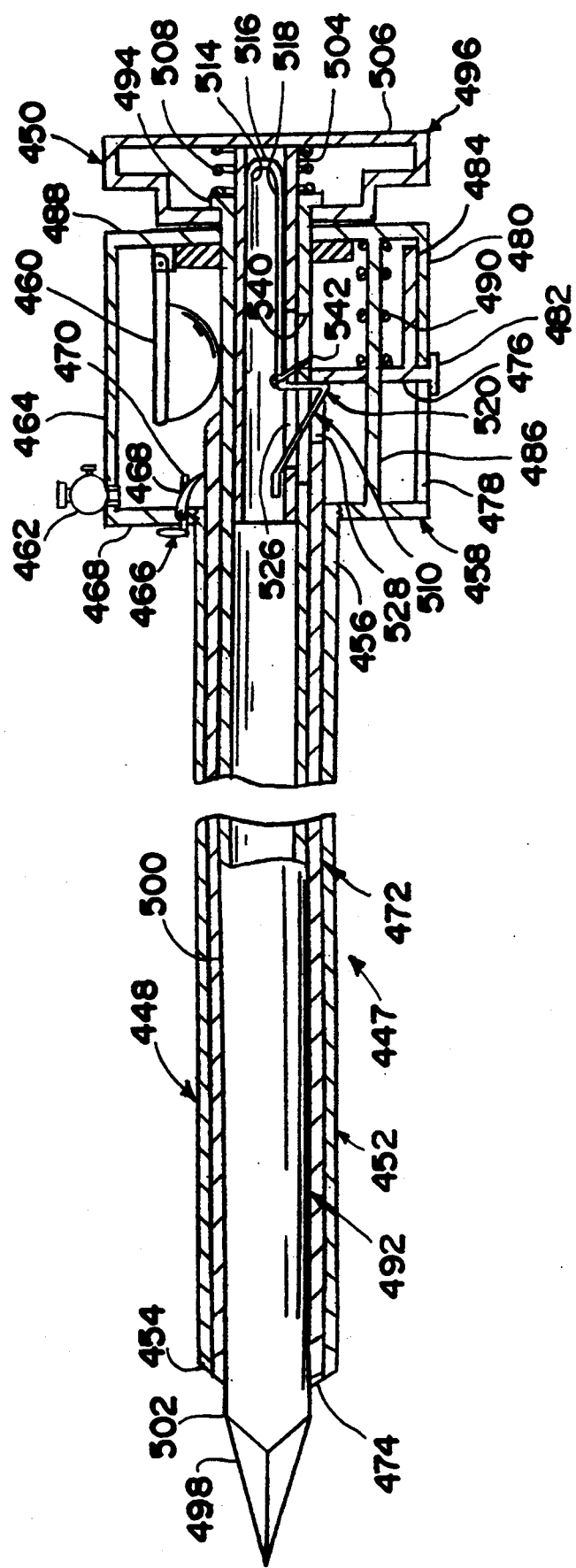
FIG. 17 is a broken longitudinal section of an additional embodiment of a safety penetration instrument according to the present invention.

An additional embodiment of a safety penetrating instrument 447 according to the present invention is shown in FIG. 17 with the primary difference between safety penetrating instruments 226 and 447 being that, in the safety penetrating instrument 447, the locking and releasing mechanism is located within the housing of the portal unit allowing the hub of the penetrating unit to have a reduced dimension between the front and rear walls. Safety penetrating instrument 447 includes a portal unit 448 and a penetrating unit 450. The portal unit 448 includes an elongate, cylindrical portal sleeve or cannula 452 having a distal end 454 and a proximal end 456 secured to a housing 458 mounting a valve 460. A stop cock 462 is mounted on a top wall 464 in communication with the housing, and a safety member locking mechanism 466 is mounted on a front wall 468 of the housing. Locking mechanism 466 includes a pawl 468 spring biased clockwise looking at FIG. 17 and a control lever 470 for releasably locking the pawl in a locking position. A safety member in the form of a shield 472 has an elongate, cylindrical configuration between a blunt distal end 474 and a proximal end received in housing 458 and carrying a flange 476 extending from the proximal end of the safety shield through a slot 478 in a bottom wall 480 of the housing to terminate at a handle 482. The handle 482 can be received in a trough-like recess as described with respect to FIG. 2 with a transparent cover sealed in the recess by a gasket surrounding the transparent cover; or, as shown in FIG. 17, a sealing member 484 can be connected with flange 476 to extend proximally therefrom a length greater than the length of slot 478 such that the sealing member 484 will seal the opening created by the slot 478. Flange 476 has an opening therein receiving a guide rod 486 extending between the front wall 468 and a rear wall 488 of the housing, and a helical spring 490 is coiled around rod 486 and mounted in compression between flange 476 and rear wall 488 of housing 458 to bias the safety shield 472 distally toward the extended position where distal end 474 protrudes beyond the sharp tip of the penetrating member.

The penetrating unit 450 includes an elongate penetrating member 492 having a proximal end terminating at a flange 494 received in a hub 496, a sharp distal end 498 and a shaft 500 extending between the proximal and distal ends, the sharp distal end 498 having facets tapering from a junction 502 with shaft 500 to a sharp point as in a conventional 3-sided trocar; however, the sharp distal end 498 can have any desired configuration. The proximal end of the penetrating member is hollow and receives a guide tube 504 extending from a rear wall 506 of hub 496 concentric with the longitudinal axis of the safety penetrating instrument to allow the penetrating member to slide over the guide tube against the bias of a helical spring 508 coiled around the guide tube and mounted in compression between flange 494 and hub rear wall 506.

Figure 18:
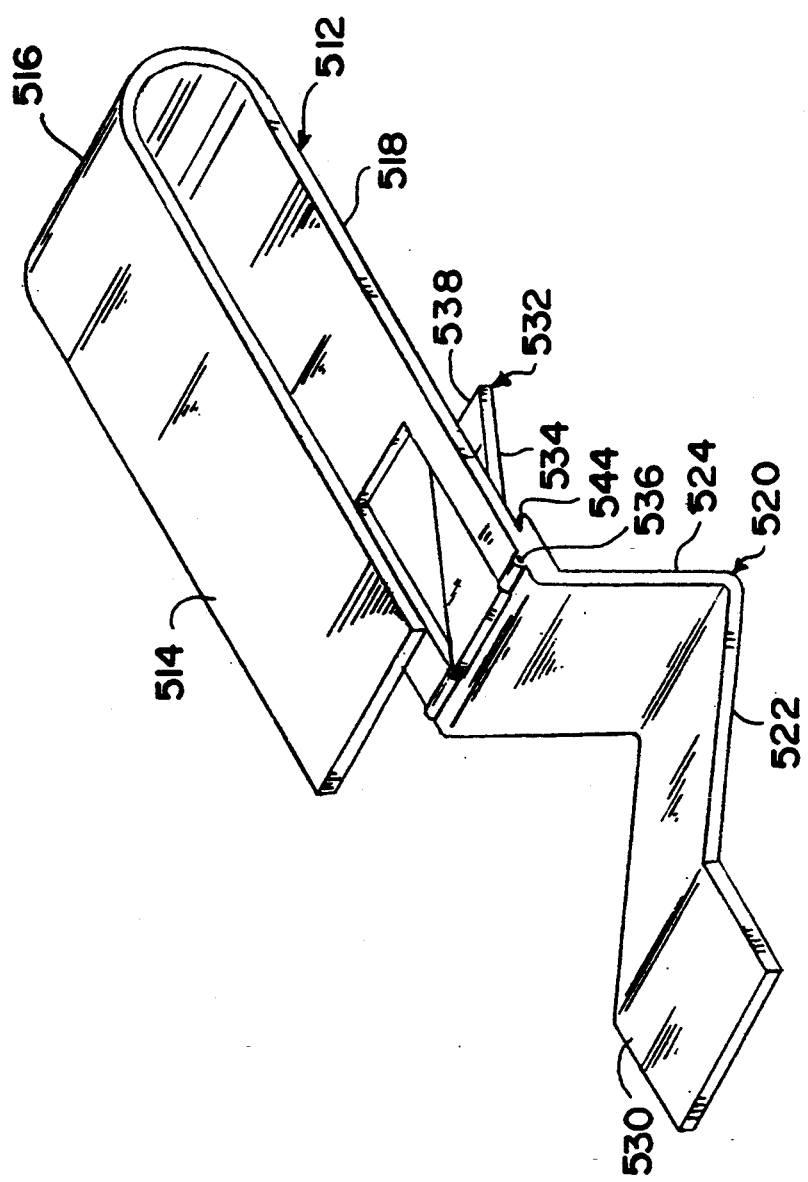
FIG. 18 is a perspective view of the locking and releasing mechanism of the modification of FIG. 17.

A locking and releasing mechanism 510 for locking the safety shield in a retracted position exposing the sharp distal end 498 of the penetrating member and for releasing the safety shield to allow the safety shield to return to the extended position protruding beyond the distal end of the penetrating member is disposed within guide tube 504 and, as shown in ]FIGS. 17 and 18, includes a latch or locking spring 512 made of a strip of resilient material formed to have a base 514 secured in guide tube 504 and a bend 516 joining the base 514 with an arm 518 spaced from the base. Arm 518 carries a protruding latch 520 having a distal angled surface 522 joining a proximal latching surface 524 disposed substantially transversely to the longitudinal axis of the safety penetrating instrument and substantially parallel to the safety shield flange 476. Latch 520 extends through a slot 526 in guide tube 504 and a slot 528 in safety shield 472 adjacent flange 476. Angled surface 522 terminates at an extension 530 disposed within guide tube 504. A trigger 532 is formed by a leg 534 having an end pivotally mounted on a pin 536 on arm 512, and an opposing end 538 of leg 534 extends angularly, proximally from arm 518 through slot 526 in guide tube 504 to be received in a slot 540 in penetrating member 492 separated from slot 528 by a portion of shaft 500 forming an operating member 542. Locking spring 512 carries a protrusion 544 disposed adjacent leg 534 of trigger 532 to limit clockwise pivotal movement of the trigger away from arm 518 while counterclockwise pivotal movement of trigger 532 is permitted against the bias of a spring, not shown.

In use, the safety penetrating instrument 446 will initially be in a position with safety shield 472 extended beyond the sharp distal end 498 of the penetrating member 492 such that flange 476 of the safety shield is adjacent the front wall 468 of housing 458 due to the bias from spring 490. In order to move the safety shield to the retracted position shown in FIG. 17, handle 482 is grasped to move the safety shield proximally, the control lever 470 having been previously moved to allow counterclockwise rotation of locking pawl 468. Proximal movement of the safety shield will move arm 518 of locking spring 512 radially inwardly by contact of flange 476 with angled surface 522. Once flange 476 has moved past latch 520, arm 518 will spring back to the position shown in FIG. 17 such that latching surface 524 engages flange 476. During penetration of an anatomical cavity wall, penetrating member 492 will move proximally until flange 494 has completely compressed spring 508 in which position junction 502 at the distal end of the penetrating member will be aligned with the distal ends of the safety shield and the sleeve. In this position, operating member 542 will have moved past trigger 532 causing the trigger to pivot counterclockwise to a position just proximal of trigger 532 without causing any movement of arm 518. Upon entry into the anatomical cavity, spring 508 will move penetrating member 492 distally causing the operating member 542 to engage leg 534 of trigger 532 pivoting the leg clockwise against protrusion 544 such that arm 518 will flex toward base 514 moving latch 520 out of engagement with flange 476 and allowing spring 490 to move the safety shield distally to the extended position. Once the safety shield has moved to the extended position, pawl 468 will be biased to a position abutting the proximal end of the safety shield and locked in place by control lever 470 to hold the safety shield in the extended position. Once penetration is complete, the penetrating member, including hub 496 and penetrating member 492, is removed from the portal unit such that the sleeve 452 and the safety shield 472 remain in place with the safety shield assuring communication with the anatomical cavity in the event that the sleeve has not been received in the anatomical cavity. To remove the penetrating member, latch 520 is depressed in any suitable manner by an extending arm or inserting an instrument through slot 478 in housing 458. It will be appreciated that with the portal unit left in place, the housing is sealed by engagement of sealing member 484 with slot 478 or by the use of a sealing gasket around a transparent cover over handle 482, the sealing being further accomplished by movement of valve 460 to be closed once the penetrating unit is withdrawn.

Figure 19:
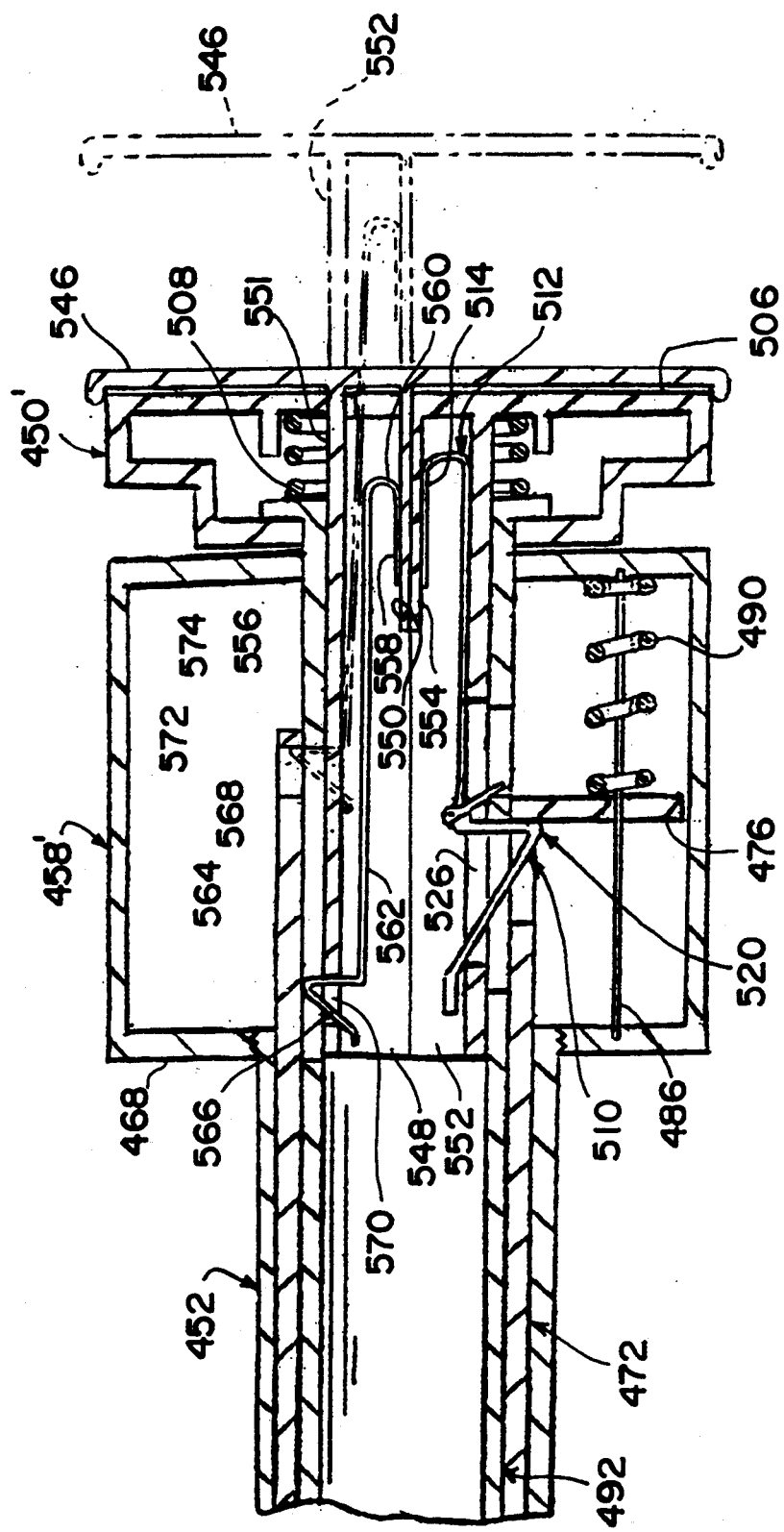
FIG. 19 is a broken longitudinal section of a modification of the safety penetrating instrument of FIG. 17 according to the present invention.

A modification of the safety penetrating instrument 447 of FIG. 17 is shown in FIG. 19 with the primary difference in the modification of FIG. 19 being that the handle for manually moving the safety member to the retracted position extends axially from the housing and hub thereby requiring no additional sealing for the housing. More particularly, a handle 546 abuts the rear wall 506 of the hub 450', and a semi-tubular support member 548 extends distally therefrom having a lower wall 550 and an upper wall 551. A semi-tubular support member 552 extends from rear hub wall 506 and has an upper wall 554 mounting the base 514 of the latching or locking spring 512 and a lower wall with slot 526 therein. Support members 548 and 552 form, together, a tubular structure having the configuration of guide tube 504 in safety penetrating instrument 447 such that penetrating member 492 slides therealong. A locking member 556 formed of a strip of spring or resilient material has a base 558 mounted on wall 550 and a bend 560 joining base 558 with an arm 562 spaced from the base and carrying a latch protrusion 564 having an angled distal surface 566 and a latching surface 568 extending substantially transversely from the longitudinal axis of the safety penetrating instrument. The handle 546 is axially movable as illustrated in phantom within the hub 450' and the housing 458', it being noted that., for purposes of simplification, the valve is housing 458' is not shown. Latching protrusion 564 extends through a slot 570 in wall 551 of support member 548 in alignment with a slot 572 in penetrating member 492. Safety shield member 472 has a slot 574 formed at the proximal end thereof for receiving latch 564.

Prior to use of the safety penetrating instrument, slot 574 in safety shield 472 is aligned with latch 564 such that the latch is received in the slot when the safety shield is in the extended position with flange 476 abutting hub front wall 468. When it is desired to move the safety shield proximally from the extended position to the retracted position, handle 546 is grasped and moved proximally to the position shown in phantom at which time latch 564 is engaged in slot 574 to move the safety shield proximally until flange 476 is engaged by latch 520 of the locking and releasing mechanism 510. Once the safety shield has been locked in the retracted position, handle 546 can be moved distally with latch 564 moving out of slot 574 to disengage the safety shield due to the angle of surface 566. Thus, with the safety penetrating instrument in the position shown in FIG. 19, penetration of an anatomical wall can be commenced with the triggering operation the same as described above with respect to safety penetrating instrument 447.

Release of the safety member to move proximally to the extended position can be triggered by movement of an operating member carried on any member movable in response to the penetrating member entering the anatomical cavity. As described above, the operating member is carried by the penetrating member to limit the number of components in the safety penetrating instrument; however, the operating member could be carried on an additional member movable in response to penetration into the anatomical cavity such as, for example, a probe or rod in or along side of the penetrating member biased to protrude slightly from the distal end of the penetrating member or a hollow member or tube in or around the penetrating member biased to protrude slightly from the distal end of the penetrating member. The safety member can have various configurations so long as the distal end protrude beyond the sharp tip of the penetrating member to provide a protective function, and a plurality of safety members can be employed in a safety penetrating instrument, for example by having a plurality of safety probes passing alongside the penetrating member or through one or more openings in hollow or solid penetrating members or by having a multi-component safety shield. Similarly, various bias means can be used in the safety penetrating instrument to produce movement of the operating member and the safety member including, for example, tension or compression coiled springs, rubber or plastic or magnets.

The components of the safety penetrating instrument of the present invention can be made of any suitable, medical grade materials to permit sterilization for reuse or for single patient use. With respect to the latter, the components can be made of multiple parts of various configurations and materials to reduce cost. The portal unit can have various valves, stop cocks, and seals in the housing to control fluid flow therethrough, and conventional detent mechanisms can be used to connect or latch the hub with the housing when the portal unit and the penetrating unit are assembled.

The locking and releasing mechanisms require only a latch for locking the safety member in the retracted position and a trigger for releasing the latch in response to distal movement of an operating member; and, thus, it will be appreciated that various mechanisms can be employed to produce the locking and releasing functions such as, for example, multiple movably or pivotally mounted cams or pawls. Various locking and releasing mechanisms that can be simply modified for use in the safety penetrating instrument of the present invention are disclosed in applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578 filed Apr. 15, 1993, Ser. No. 07/929,338, filed Aug. 14, 1992 and Ser. No. 07/845,177, filed Sep. 15, 1992, the disclosures of which are incorporated herein by reference. The above applications disclose automatically retracting safety penetrating instruments such that modification of the locking and releasing mechanisms requires configuring the latches to lock a member in a retracted position rather than an extended position. The above applications also disclose various bias arrangements useful with the safety penetrating instrument of the present invention.

From the above, it will be appreciated that the safety penetrating instrument of the present invention permits use of strong bias springs to assure movement of the safety member to the extended, protective position without increasing the force to penetrate. Further, after penetration of the safety penetrating instrument into the anatomical cavity, the safety member acts as a shock absorber upon inadvertent contact with tissue which contact can be felt by the surgeon and visually determined by movement of the handle. Additionally, the safety penetrating instrument can be used as a standard trocar, a standard safety shielded trocar or a triggered safety shielded trocar without required complex mechanisms. The features of the various embodiments described above can be combined in any manner desired dependent upon the requirements and complexity of the safety penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in a wall of an anatomical cavity for performing endoscopic procedures comprising
    an elongate, tubular portal sleeve having a distal end for positioning in the anatomical cavity and a proximal end for positioning externally of the anatomical cavity wall;
    a penetrating member disposed in said portal sleeve having a distal end for penetrating tissue;
    a safety member disposed within said portal sleeve and having a distal end, said safety member being movable relative to said penetrating member and said portal sleeve between an extended position where said safety member distal end protrudes distally from said penetrating member distal end and said portal sleeve distal end and a retracted position where said safety member distal end is disposed proximally of said penetrating member distal end to expose said penetrating member distal end;
    bias means for biasing said safety member to move distally toward said extended position and for permitting said safety member to move proximally toward said retracted position;
    handle means coupled with said safety member for manually moving said safety member proximally relative to said portal sleeve from said extended position to said retracted position;
    locking means for engaging said safety member to prevent distal movement of said safety member from said retracted position to said extended position; and
    releasing means responsive to entry of said safety penetrating instrument into the anatomical cavity for triggering release of said locking means to permit said bias means to move said safety member to said extended position.

2. A safety penetrating instrument as recited in claim 1 wherein said penetrating member has a proximal end and said safety member has a proximal end and further comprising hub means receiving said penetrating member proximal end and said safety member proximal end whereby said penetrating member and said safety member can be withdrawn from said portal sleeve together by grasping said hub means.

3. A safety penetrating instrument as recited in claim 2 wherein said handle means extends from said hub means and said locking means is disposed in said hub means at a position to automatically lock said safety member in said retracted position when said safety member is manually moved to said retracted position by said handle means.

4. A safety penetrating instrument as recited in claim 3 and further comprising control means coupled with said locking means for moving said locking means to prevent automatic locking of said safety member in said retracted position whereby said safety member can move proximally without locking in said retracted position.

5. A safety penetrating instrument as recited in claim 2 wherein said hub means includes a wall having a slot therein and said handle means includes a pin extending through said slot to terminate at a handle external of said hub means to be visible.

6. A safety penetrating instrument as recited in claim 5 wherein said hub means includes a transparent cover disposed over said slot and said handle.

7. A safety penetrating instrument as recited in claim 2 wherein said safety penetrating instrument has a longitudinal axis, said hub means includes a rear wall with a passage therethrough and said handle means includes a member extending through said passage for movement substantially along said longitudinal axis of said safety penetrating instrument.

8. A safety penetrating instrument as recited in claim 1 wherein said safety member distal end extends around said penetrating member sharp distal end.

9. A safety penetrating instrument as recited in claim 1 wherein said safety member distal end extends through said penetrating member sharp distal end.

10. A safety penetrating instrument as recited in claim 1 wherein said portal sleeve has a proximal end and said safety member has a proximal end and further comprising housing means receiving said portal sleeve proximal end and said safety member proximal end, said penetrating member passing through said housing means whereby said penetrating member can be withdrawn from said portal sleeve leaving said safety member within said portal sleeve.

11. A safety penetrating instrument as recited in claim 10 wherein said locking means and said releasing means are disposed in said housing means.

12. A safety penetrating instrument as recited in claim 11 wherein said handle means extends from said housing means and further comprising sealing means for preventing fluid flow from said housing means adjacent said handle means.

13. A safety penetrating instrument as recited in claim 10 and further comprising a protective sheath surrounding said penetrating member and having a distal end and protective sheath bias means for biasing said protective sheath to move to an extended position where said protective sheath distal end protrudes beyond said penetrating member sharp distal end.

14. A safety penetrating instrument as recited in claim 1 wherein said penetrating member has a proximal end and further comprising hub means receiving said penetrating member proximal end, said locking means and said releasing means being disposed within said penetrating member between said hub means and said penetrating member sharp distal end.

15. A safety penetrating instrument as recited in claim 1 and further comprising hub means mounting said penetrating member and penetrating member bias means biasing said penetrating member distally and permitting proximal movement of said penetrating member with respect to said hub means and wherein said releasing means includes an operating member coupled with said penetrating member for triggering release of said locking means when said penetrating member bias means moves said penetrating member distally upon penetration into the anatomical cavity.

16. A safety penetrating instrument as recited in claim 1 and further comprising means for locking said safety member in said extended position.

17. A safety penetrating instrument for establishing a portal in a wall of an anatomical cavity for performing endoscopic procedures comprising an elongate, tubular portal sleeve having a distal end for positioning in the anatomical cavity and a proximal end for positioning externally of the anatomical cavity wall;

a penetrating member disposed in said portal sleeve having a distal end for penetrating tissue and a proximal end;

hub means receiving said penetrating member proximal end;

penetrating member bias means for biasing said penetrating member distally relative to said hub means and permitting proximal movement of said penetrating member relative to said hub means in response to a force on said penetrating member distal end;

a safety member disposed within said portal sleeve and having a distal end, said safety member being movable relative to said penetrating member and said portal sleeve between an extended position where said safety member distal end protrudes distally from said penetrating member distal end and said portal sleeve distal end and a retracted position where said safety member distal end is disposed proximally of said penetrating member distal end to expose said penetrating member distal end;

safety member bias means for biasing said safety member to move distally toward said extended position and for permitting said safety member to move proximally toward said retracted position;

locking means for engaging said safety member to prevent distal movement of said safety member from said retracted position to said extended position; and releasing means responsive to entry of said safety penetrating instrument into the anatomical cavity for triggering release of said locking means to permit said safety member bias means to move said safety member to said extended position.

18. A safety penetrating instrument as recited in claim 17 wherein said releasing means includes an operating member carried by said penetrating member for triggering release of said locking means upon said penetrating member bias means moving said penetrating member distally when said penetrating member enters the anatomical cavity.

19. A safety penetrating instrument as recited in claim 17 wherein said penetrating member has a proximal end and said safety member has a proximal end and wherein said hub means receives said penetrating member proximal end and said safety member proximal end whereby said penetrating member and said safety member can be withdrawn from said portal sleeve together by grasping said hub means.

20. A safety penetrating instrument as recited in claim 17 wherein said safety member distal end extends around said penetrating member sharp distal end.

21. A safety penetrating instrument as recited in claim 17 wherein said safety member distal end extends through said penetrating member sharp distal end.

22. A safety penetrating instrument as recited in claim 17 wherein said portal sleeve has a proximal end and said safety member has a proximal end and further comprising housing means receiving said portal sleeve proximal end and said safety member proximal end, said penetrating member passing through said housing means whereby said penetrating member can be withdrawn from said portal sleeve leaving said safety member within said portal sleeve.

23. A safety penetrating instrument for establishing a portal in a wall of an anatomical cavity for performing endoscopic procedures comprising an elongate, tubular portal sleeve having a distal end for positioning in the anatomical cavity and a proximal end for positioning externally of the anatomical cavity wall;

a penetrating member disposed in said portal sleeve having a distal end for penetrating tissue;

a safety member disposed within said portal sleeve and having a distal end, said safety member being movable relative to said penetrating member and said portal sleeve between an extended position where said safety member distal end protrudes distally from said penetrating member distal end and said portal sleeve distal end and a retracted position where said safety member distal end is disposed proximally of said penetrating member distal end to expose said penetrating member distal end;

bias means for biasing said safety member to move distally toward said extended position and for permitting said safety member to move proximally toward said retracted position;

locking means for engaging said safety member in said retracted position to prevent distal movement of said safety member relative to said portal sleeve such that said safety member cannot move from said retracted position to said extended position; and releasing means including an operating member movable distally responsive to entry of said safety penetrating instrument into the anatomical cavity for triggering release of said locking means to permit said bias means to move said safety member to said extended position.

24. A safety penetrating instrument for establishing a portal in a wall of an anatomical cavity for performing endoscopic procedures comprising an elongate, tubular portal sleeve having a distal end for positioning in the anatomical cavity and a proximal end for positioning externally of the anatomical cavity wall;

a penetrating member disposed in said portal sleeve having a distal end for penetrating tissue;

a safety member disposed within said portal sleeve and having a distal end, said safety member being movable relative to said penetrating member and said portal sleeve between an extended position where said safety member distal end protrudes distally from said penetrating member distal end and said portal sleeve distal end and a retracted position where said safety member distal end is disposed proximally of said penetrating member distal end to expose said penetrating member distal end;

bias means for biasing said safety member to move distally toward said extended position and for permitting said safety member to move proximally toward said retracted position;

handle means coupled with said safety member for manually moving said safety member proximally relative to said portal sleeve from said extended position to said retracted position;

locking means for engaging said safety member to lock said safety member in said retracted position; and releasing means responsive to entry of said safety penetrating instrument into the anatomical cavity for triggering release of said locking means to permit said bias means to move said safety member to said extended position.

* * * * *